United States Patent
Mann et al.

(10) Patent No.: US 8,554,329 B1
(45) Date of Patent: Oct. 8, 2013

(54) PERCUTANEOUS COCHLEAR IMPLANT SYSTEMS AND METHODS

(75) Inventors: Alfred E. Mann, Las Vegas, NV (US); Matthew I. Haller, Valley Village, CA (US); Tom Xiaohai He, Simi Valley, CA (US)

(73) Assignee: Advanced Bionics, Valencia, CA (US)

( * ) Notice: Subject to any disclaimer, the term of this patent is extended or adjusted under 35 U.S.C. 154(b) by 552 days.

(21) Appl. No.: 12/816,142

(22) Filed: Jun. 15, 2010

Related U.S. Application Data

(60) Provisional application No. 61/187,621, filed on Jun. 16, 2009, provisional application No. 61/224,211, filed on Jul. 9, 2009.

(51) Int. Cl.
 *H04R 25/00* (2006.01)
(52) U.S. Cl.
 USPC .............................................. 607/57; 607/56
(58) Field of Classification Search
 USPC ....................................................... 607/55–57
 See application file for complete search history.

(56) References Cited

U.S. PATENT DOCUMENTS

| | | | | |
|---|---|---|---|---|
| 4,063,048 A | * | 12/1977 | Kissiah, Jr. ..................... | 607/57 |
| 4,400,590 A | * | 8/1983 | Michelson ...................... | 607/57 |
| 6,473,651 B1 | * | 10/2002 | Kuzma et al. ................... | 607/57 |
| 2005/0267549 A1 | * | 12/2005 | Della Santina et al. ......... | 607/57 |
| 2006/0264897 A1 | * | 11/2006 | Lobl et al. ..................... | 604/506 |
| 2007/0156202 A1 | * | 7/2007 | Zierhofer ........................ | 607/57 |
| 2008/0009918 A1 | * | 1/2008 | Zierhofer et al. ............... | 607/57 |

* cited by examiner

*Primary Examiner* — Kennedy Schaetzle
*Assistant Examiner* — Erica Lee
(74) *Attorney, Agent, or Firm* — Mary Elizabeth Bush

(57) ABSTRACT

A percutaneous cochlear implant system includes a cochlear stimulator configured to be coupled to an electrode lead, the electrode lead comprising a plurality of electrodes configured to be in communication with a plurality of stimulation sites within a cochlear region of a patient, a sound processor communicatively coupled to the cochlear stimulator and configured to control the cochlear stimulator to generate and apply electrical stimuli representative of an audio signal to at least one of the stimulation sites via at least one of the electrodes, a power source configured to provide power to at least one of the cochlear stimulator and the sound processor, and a percutaneous port configured to be percutaneously implanted within a head of the patient. The percutaneous port may be configured to house at least one of the power source, sound processor, and cochlear stimulator. Additionally or alternatively, the percutaneous port is configured to facilitate programming, recharging of a rechargeable power source (e.g., implanted battery), control of, and/or access to at least one of the power source, sound processor, and cochlear stimulator.

11 Claims, 36 Drawing Sheets

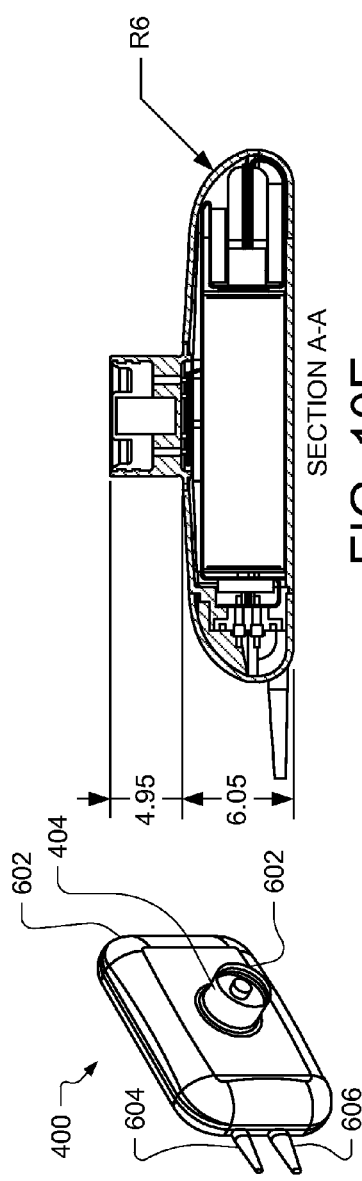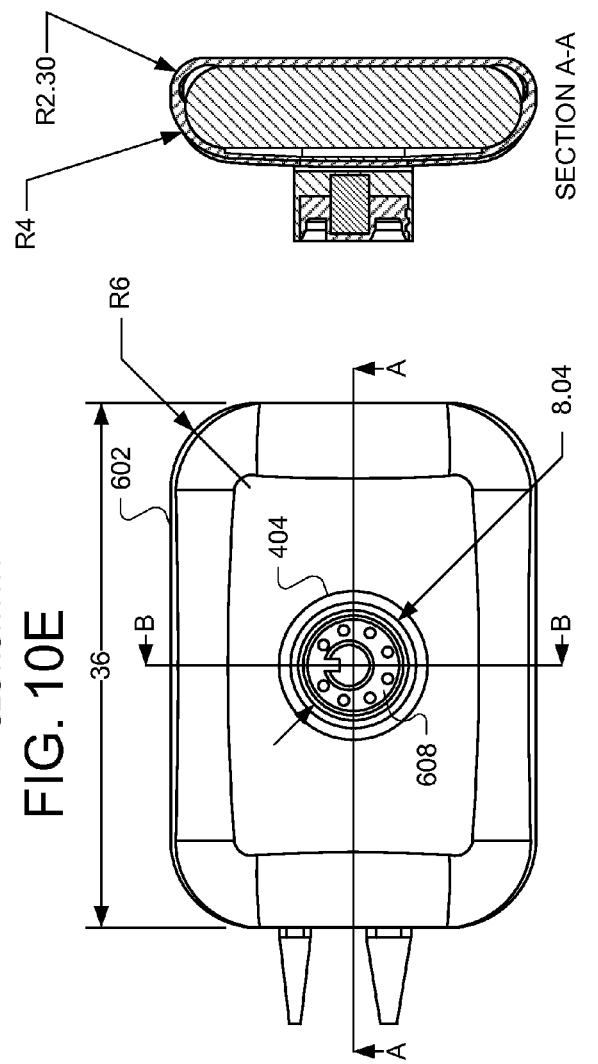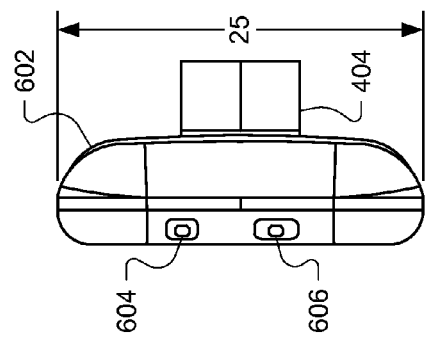

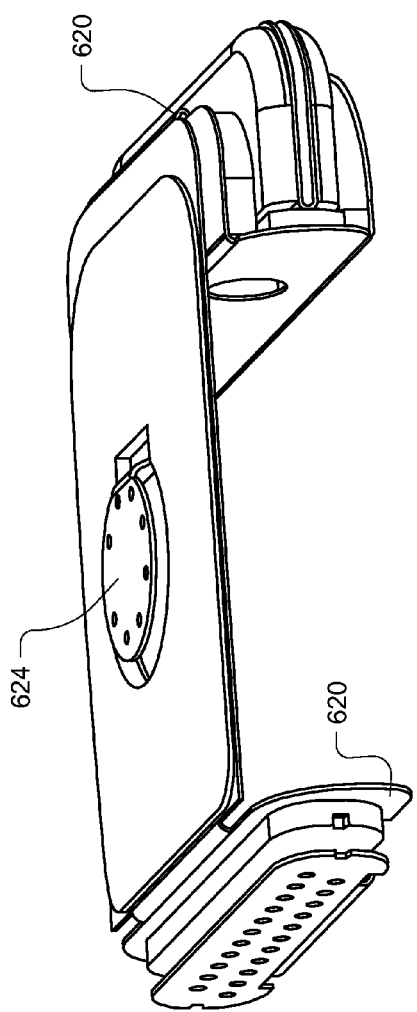
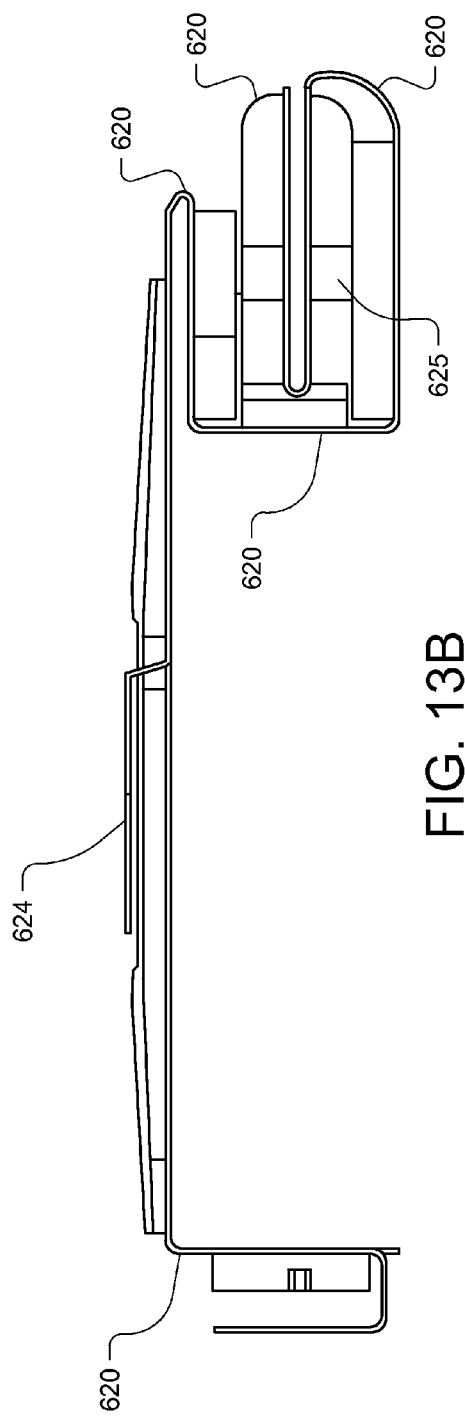
FIG. 13A
FIG. 13B

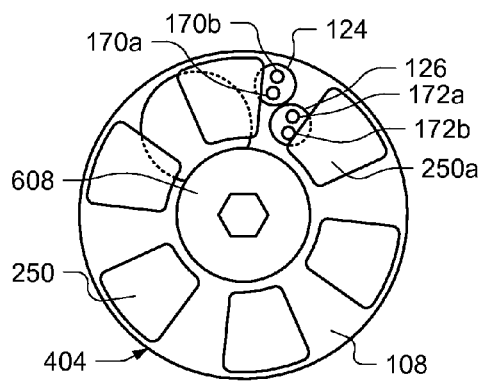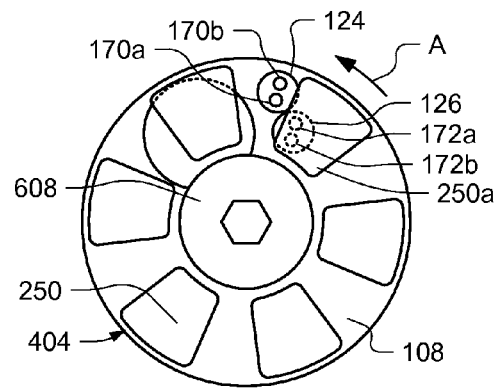
FIG. 30　　　　　　FIG. 31
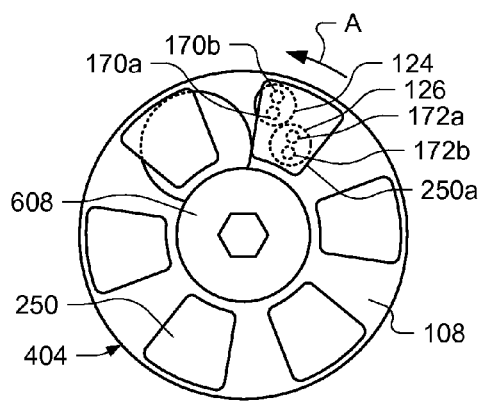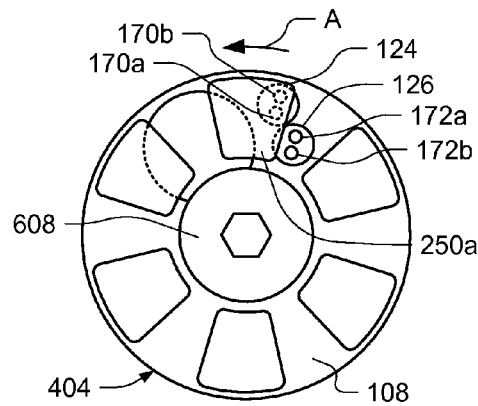
FIG. 32　　　　　　FIG. 33
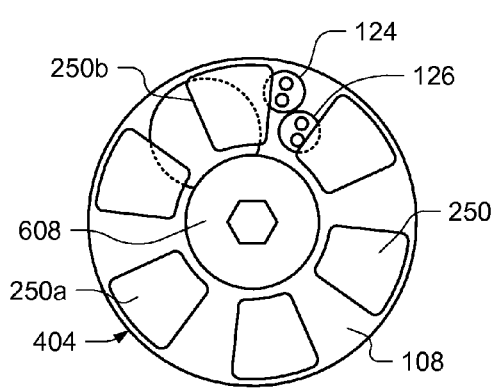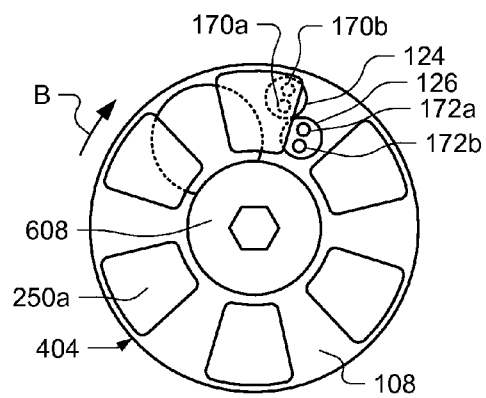
FIG. 34　　　　　　FIG. 35

PERCUTANEOUS COCHLEAR IMPLANT SYSTEMS AND METHODS

The present application claims the benefit of U.S. Provisional Patent Application Ser. No. 61/187,612, filed Jun. 16, 2009, and U.S. Provisional Patent Application Ser. No. 61/224,211, filed Jul. 9, 2009, both of which patent applications are incorporated herein by reference.

FIELD OF THE INVENTION

The present invention relates to cochlear implant systems and methods, and more particularly to a cochlear implant system and method that utilizes a direct, electrical percutaneous port embedded in the skin of the user (or patient) to enable the efficient transfer of power and data from an external (non-implanted) portion of the system to an implanted portion of the system.

More particularly, in accordance with one configuration of the invention, the use of such a percutaneous port allows the transfer of power and/or data without the use of RF telemetry and/or inductively coupled components, thereby facilitating a cochlear implant system having a smaller size and lower power consumption than has heretofore been realizable.

Even more particularly, in accordance with another configuration of the invention, a fully implantable cochlear implant system may be readily realized by using a percutaneous port as: (1) a means for channeling energy and programming data from external sources into implanted components of the system during recharging or programming modes of operation; and (2) a means for allowing manual control of the cochlear implant system during normal modes of operation.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive much if any benefit from conventional hearing aid systems. To overcome sensorineural hearing loss, numerous cochlear implant systems, or cochlear prostheses, have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

Cochlear implant systems typically include a cochlear stimulator that is implanted beneath the scalp of a patient. (Note, as used herein, "patient" is used as a synonym for "user" of a cochlear implant system.) An external assembly located external to the patient's scalp includes a microphone to receive sound signals, and sound processing circuitry as well as a battery to power the implanted cochlear stimulator. The external control assembly is also typically used to control and adjust various operational parameters of the implanted cochlear stimulator. An inductive link is used to transmit telemetry signals from the external control assembly to the implanted cochlear stimulator. Power is typically transferred through the scalp to the implanted cochlear stimulator via the inductive link. The external control assembly is often housed within a behind-the-ear (BTE) unit and/or within a carrying case that can be attached to clothing worn by the patient.

Conventional cochlear implant systems are described, e.g., in U.S. Pat. Nos. 4,267,410; 4,532,930; 5,569,307; and 6,842,647, incorporated herein by reference.

Cochlear implant systems use one or more batteries housed within their external assemblies to provide operating power for both the external circuits, e.g., speech processing circuits, and the implanted circuits, e.g., cochlea stimulating circuits. The implanted stimulation electronics have heretofore been powered by transmission from the external module. Such batteries are typically large, bulky, and relatively heavy due to the fact they must have sufficient capacity, and hence be sufficiently large, to provide operating power for extended periods of time. Implanted rechargeable batteries have not heretofore been a viable alternative for powering the implanted module or a cochlear system because there has been no efficient and convenient way to carry out the recharging function. Moreover, heretofore such batteries have degraded in use so that long-term implants would have been limited due to battery loss. Another disadvantage of a system with an implanted rechargeable battery that is recharged by rf telemetry is that the inefficient power transfer causes heating of tissue so that recharging currents must be small and the recharge time long to avoid excessive heating of tissue.

A drawback associated with conventional cochlear implant systems is that they are typically limited to a specific physical configuration, particularly with respect to the implanted components. Once a cochlear implant patient has been fitted with a cochlear implant system, the patient typically has to have the system surgically removed in order to change its physical configuration. Such procedures are invasive, costly, and undesirable.

Yet another drawback associated with conventional cochlear implant systems is that the relatively large external components thereof are readily noticeable to others and lack aesthetic appeal. Moreover, it is difficult to maintain an active lifestyle while wearing the external components because the components may fall off, become damaged, or otherwise malfunction.

It is thus seen that there is a need in the art for a cochlear implant system that overcomes the above-described drawbacks of conventional cochlear implant systems.

A percutaneous cochlear implant system is described in U.S. Pat. No. 4,400,590. However, in use, such system left an opening in the patient's skin through which infection could easily enter. Thus, because infection was a continual risk, use of a percutaneous cochlear implant system of the type described in U.S. Pat. No. 4,400,590 was effectively abandoned over 25 years ago.

Hence, it is further seen that there is a need in the art for a percutaneous cochlear implant system wherein the risk of infection is greatly reduced or eliminated.

SUMMARY

The present invention addresses the above and other needs by providing a cochlear implant (CI) system that utilizes a viable "percutaneous port" for allowing direct electrical connection through the skin without the risk of infection that has heretofore plagued percutaneous connections. The percutaneous port, also referred to herein as a "percuport", resembles a shallow thimble in shape, with the open, or proximal, end of the port being accessible from the outside of the skin, but with the port being inserted into the skin so only a lip of the port's proximal end extends above the skin. Outside a wall of the percutaneous port is a sheath bonded to the wall that is made from a fine metal mesh, e.g., a titanium mesh, as described more fully below. Because titanium is compatible with body tissue, tissue ingrowth occurs in the mesh. This is the desired consequence because such ingrowth effectively holds the percuport in place and seals the mesh with new-grown skin and vascularized tissue. A bottom, or distal, end of the percuport typically includes a ceramic, or other insulative material, through which a multiplicity of feed-through pins extend. Such feed-through pins are not limited to extending through the bottom or distal end of the percuport, but can also extend through the walls of the percuport, as a particular design or application may dictate.

There are several configurations or embodiments of a percutanious cochlear implant system made in accordance with the present inventions.

One embodiment includes a percuport into which a battery may be removably inserted. (Note, as used herein, "removably inserted" or "removably placed" or "removably located" means that a first item may be positioned inside or on a second item, and then subsequently be removed from the second item so that the first item can be reconditioned, refurbished, renewed, recharged, replaced or otherwise handled, and thereafter the reconditioned, refurbished, renewed, recharged or replaced first item may be returned to its previous location inside or on the second item.) A container or housing for a CI circuit assembly resides at the side of the percuport, flexibly connected thereto so that the percuport and container may better conform to the skull curvature. Alternatively, the CI circuit assembly may reside below the percuport. Feed-through pins (also referred to herein as "feedthrus") provide electrical connection between the circuitry housed in the container and electrodes adapted for insertion into the cochlea. Such cochlear electrodes reside at or near the distal end of an electrode lead.

Another embodiment of a CI system made in accordance with the present inventions comprises a fully implantable system that includes an implantable rechargeable battery and a container (or housing) wherein the CI circuits reside. The implantable battery may reside in the same container wherein the CI circuits reside, or in a separate container flexibly connected to the CI circuits. A percuport is connected to the battery and CI circuits. When recharging the battery, or reprogramming the CI circuits, external units that perform the recharging or programming function may connect directly with the implanted battery and CI circuits through a cable having a plug at its distal end that is inserted into the percuport.

In one variation of this fully implantable embodiment, a recharging module is directly connected to the implanted unit through the percuport plug.

In another variation of this fully implantable embodiment, during normal operation (i.e., when not recharging or reprogramming), a cover plug (which does not have a cable or wires connected to it) is inserted into the percuport. Rotation of the cover plug relative to the percuport allows a user of the CI system to manually control some basic functions associated with operation of the CI system, such as on/off, volume, sensitivity and the like.

In accordance with yet another variation of this fully implantable embodiment, a plug having a wireless receiver embedded therein, such as a Bluetooth® receiver, receives control signals from a remote control unit and sends such signals through the percuport to the CI circuits. This allows the user, through use of the remote control, to control some basic functions of the CI system, such as on/off, volume, sensitivity and the like.

Numerous configurations or embodiments of the percutaneous cochlear implant system (PCIS) described herein allow different combinations of components of the PCIS to be either permanently implanted or not implanted, as needed, to suit the needs of a particular design or application. The non-implantable components can be readily replaced or removed, as needed, and replaced with new, upgraded or recharged components.

Thus, it is seen that in operation and use, implantable components of the PCIS attach to the implanted, or distal, side of the feedthrus, while non-implantable components of the PCIS, e.g., a battery (in some embodiments), or test/programming cables, connect to the non-implanted, or proximal, side of the feedthrus. Such non-implantable components, in some embodiments, may advantageously fit within the percuport so as make necessary contact with the proximal side of the feedthrus located at or near the distal end of the percuport. Other embodiments may place such implantable components some distance away from the percuport, but connected to the feedthrus thereof through suitable cabling.

Thus, a percutaneous cochlear implant system made as described herein includes a cochlear stimulator configured to be coupled to an electrode lead, the electrode lead comprising a plurality of electrodes configured to be in communication with a plurality of stimulation sites within a cochlear region of a patient, a sound processor communicatively coupled to the cochlear stimulator and configured to direct the cochlear stimulator to generate and apply electrical stimuli representative of an audio signal to at least one of the stimulation sites via at least one of the electrodes, a power source configured to provide operating power to at least one of the cochlear stimulator and the sound processor, and a percutaneous port configured to be percutaneously implanted within the tissue of the patient, e.g., within the head of the patient. The percutaneous port is configured to house at least a set of feedthrus that allow electrical communication between external components and implantable components of the CI system. It may also, in some embodiments, hold or house other components of the CI system, such as a power source and/or portions or all of the sound processor circuits.

It is a feature of the system herein described to provide a cochlear implant system wherein some components of the system are implanted and some components of the system are non-implanted, and wherein the required electrical or signal links between the implanted components and non-implanted components are made through a percutaneous port embedded in the skin of a user of the system.

It is another feature of the system herein described to provide a cochlear implant system that does not require radio frequency telemetry nor inductive coupling to provide a communicative link for power and/or data signals between the implanted portions of the system and the non-implanted portions of the system.

If is still a further feature of the cochlear implant system described herein to provide both implanted components and non-implanted components coupled together through a percutaneous port, and wherein the percutaneous port is configured to allow tissue ingrowth and vascularization, which tissue ingrowth and vascularization provides a very effective barrier to infection.

Yet another feature of the system herein described is to provide a modular-based cochlear implant system wherein different component groupings or modules provide different embodiments suited for different applications or needs. In one embodiment or configuration, for example, most components of the system may be implanted and only a few components of the system (such as a programming/testing module and recharging module) are non-implanted. In another embodiment or configuration, most components of the system may be non-implanted and only a few components of the system (such as an electrode lead) are implanted. In this manner, a full spectrum of possible embodiments and configurations of the cochlear implant system—ranging from a system that is almost fully implanted to a system that is mostly non-implanted—may be designed and fabricated in order to best meet the needs and demands of a particular patient group or application.

As an additional feature of the system herein described, in accordance with one aspect thereof, there is disclosed a cochlear implant system having implantable and non-implantable components electrically coupled together through a percutaneous port, wherein existing, approved and fully tested implantable components may be used in implantable modules or housings, and existing, approved and tested non-implantable components may be used in non-implantable modules, housings or configurations, to thereby shorten the time required to obtain regulatory approval for the cochlear implant system as a whole.

BRIEF DESCRIPTION OF THE DRAWINGS

The above and other aspects, features and advantages of the percutaneous cochlear implant system described herein will be more apparent from the following more particular description thereof, presented in conjunction with the accompanying drawings. These drawings illustrate various embodiments of the principles described herein and are a part of the specification. The illustrated embodiments are merely examples and do not limit the scope of the disclosure.

FIG. 10 shows, starting in the upper left hand corner and proceeding counter-clockwise: (FIG. 10A) an alternate perspective view of the fully implantable PCIS of FIG. 9; (FIG. 10B) a side view; (FIG. 10C) a top view; (FIG. 10D) a sectional view taken along the lines B-B; and (FIG. 10E) a sectional view taken along the lines A-A.

FIG. 13 shows an ISO view (FIG. 13A) and side (FIG. 13B) view of the PCIS shown in FIG. 10 with the covers, case and battery removed, and shows the manner in which a folded flex printed circuit board (PCB) fits over and around the battery.

FIGS. 30-35 are plan views showing a plurality of sensible members moving relative to a pair of sensors contained within a bottom edge of a percutaneous port, wherein being able to sense the location of the sensible members provides a manual user interface that allows a user the ability to generate control signals for controlling at least some functions of the PCIS through manual rotation of a cartridge, on which the sensible members are placed, inserted into the percutaneous port.

Throughout the drawings, identical reference numbers designate similar, but not necessarily identical, elements. Hence, it is to be understood that the features illustrated in a specific drawing are not to be limited to just the configuration of the invention illustrated in that specific drawing, but rather such features have wide applicability to all configurations and embodiments of the invention.

DETAILED DESCRIPTION

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
   I. Introduction and Overview
   II. Exemplary Percutaneous Port
   III. Exemplary Cochlear Implant Systems utilizing a Percutaneous Port
   IV. Exemplary Percutaneous Cochlear Implant System (PCIS) Having All Operative Components Implanted
   V. Exemplary Manual Control Methodologies
   VI. Additional Exemplary Implementations The section titles and overall organization of the present detailed description are for the purpose of convenience only and are not intended to limit the present inventions.

I. Introduction and Overview

Figure 1A:
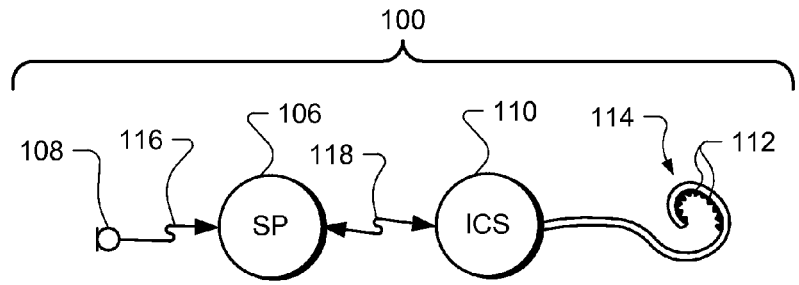
FIG. 1A illustrates the main implantable and non-implantable components of an exemplary conventional cochlear implant system.

FIG. 1A illustrates an exemplary cochlear implant system 100. Cochlear implant system 100 may include, but is not limited to, a sound processor 106, a microphone 108, a cochlear stimulator 110, a number of electrodes 112 disposed on an electrode lead 114, and/or additional circuitry as best serves a particular application. Typically, in a conventional cochlear implant system of the type that has heretofore been used, the sound processor 106 and microphone 108 are external, or non-implanted, while the cochlear stimulator 110 and electrode lead 114 are implanted. It should be noted, however, that these external/implanted relationships can vary depending upon the needs of a particular application.

The microphone 108 of FIG. 1A is configured to sense audio signals and convert the sensed signals to corresponding electrical signals. In some examples, the audio signal may include speech. The audio signal may additionally or alternatively include music, noise, and/or other sounds. The electrical signals are transmitted from microphone 108 to sound processor 106 via a communication link 116, which may include a telemetry link, a wire, and/or any other type of communication link 116 as may serve a particular application. In conventional systems the microphone is external and coupled electrically and usually mechanically to the processor. In some examples of the current invention, microphone 108 may be located external to the patient. Alternatively, microphone 108 may be placed within the ear canal of the patient, or in some other suitable location on the patient where sound can be readily perceived.

Sound processor 106 is configured to process the converted audio signals in accordance with a selected sound processing strategy. Based on the selected sound processing strategy, appropriate stimulation parameters are generated for controlling cochlear stimulator 110, which may be implanted within the patient. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by cochlear stimulator 110.

Sound processor 106 and cochlear stimulator 110 may be communicatively coupled via a suitable data or communication link 118. It will be understood that data communication link 118 may include a bi-directional communication link and/or one or more dedicated uni-directional communication links.

In a conventional cochlear implant system, the communicative link 118 is realized through inductive or RF coupling. That is, inductive coupling established between an external coil and an implanted coil allows a carrier signal to be transmitted from the external components to the implanted components. This carrier signal, when received on the implanted side, is rectified and filtered and provides operating power for the implanted components. Control data is typically sent from the external components to the implanted components by modulating the carrier signal using an appropriate modulation scheme. Back telemetry signals may be sent from the implanted components of the system to the external components of the system via RF telemetry.

Electrode lead 114 shown in FIG. 1 is configured to be inserted within a duct of a cochlea. As shown in FIG. 1A, electrode lead 114 includes a plurality of electrodes 112, e.g., sixteen electrodes, spaced along its length. It will be understood, however, that any number of electrodes 112 may be disposed on electrode lead 114. Electronic circuitry within cochlear stimulator 110 is configured to generate and apply electrical stimulation to one or more stimulation sites within the cochlea via selected stimulation channels (i.e., pairs or groups of individual electrodes 112) in accordance with a specified stimulation strategy defined by sound processor 106. Hence, one or more electrode leads 114 with one or more electrodes 112 disposed thereon may be implanted within a patient such that electrodes 112 are in communication with one or more stimulation sites within the patient. As used herein, the term "in communication with" refers to electrodes 112 being adjacent to, in the general vicinity of, in close proximity to, directly next to, or directly on the stimulation site.

Figure 1B:
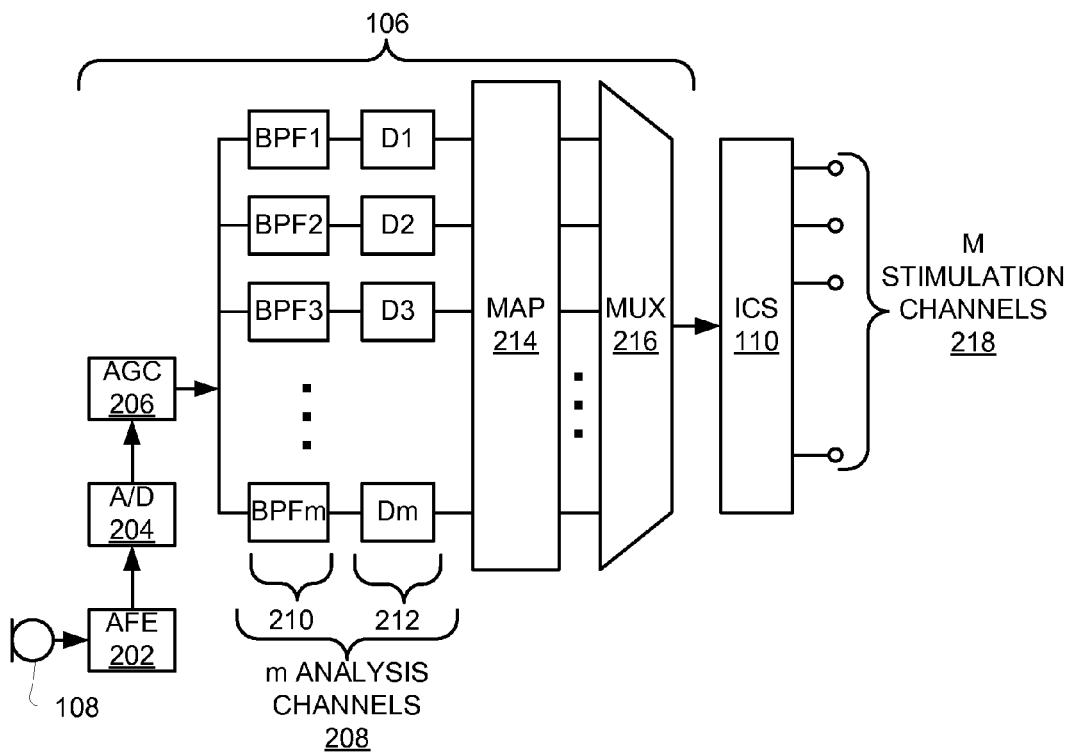
FIG. 1B is a functional block diagram of an exemplary cochlear stimulator system.

FIG. 1B shows a functional block diagram of an exemplary sound processor 106 and cochlear stimulator 110. The functions shown in FIG. 1B are merely representative of the many different functions that may be performed by the sound processor 106 and/or the cochlear stimulator 110.

As shown in FIG. 1B, microphone 108 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) function 206.

After appropriate automatic gain control, the digital signal is then processed in one of a number of digital signal processing or analysis channels 208. For example, sound processor 106 may include, but is not limited to, eight or 16 or 22 or any number of analysis channels 208. Each analysis channel 208 may respond to a different frequency band of the sensed audio signal due to a group of band pass filters 210 through which the processed signal is subjected.

As shown in FIG. 1B, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include some type of envelope detection circuit, such as a rectification circuit followed by an integrator circuit, to detect the amount of energy contained within the signal present in the analysis channel 208.

After energy detection, the signals within each of the m analysis channels 208 are forwarded to a mapping stage 214. Mapping stage 214 is configured to map the signals in each of the m analysis channels 208 to one or more of M stimulation channels 218. In other words, the information contained in the m analysis channels 208 is used to define the electrical stimulation pulses that are applied to the patient by cochlear stimulator 110 via the M stimulation channels 218. As mentioned previously, pairs or groups of individual electrodes 112 may make up the M stimulation channels 218.

In some embodiments, the mapped signals are serialized by a multiplexer 216 and transmitted to the cochlear stimulator 110. The cochlear stimulator 110 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue (e.g., auditory nerve tissue 306 shown in FIG. 10).

Figure 1C:
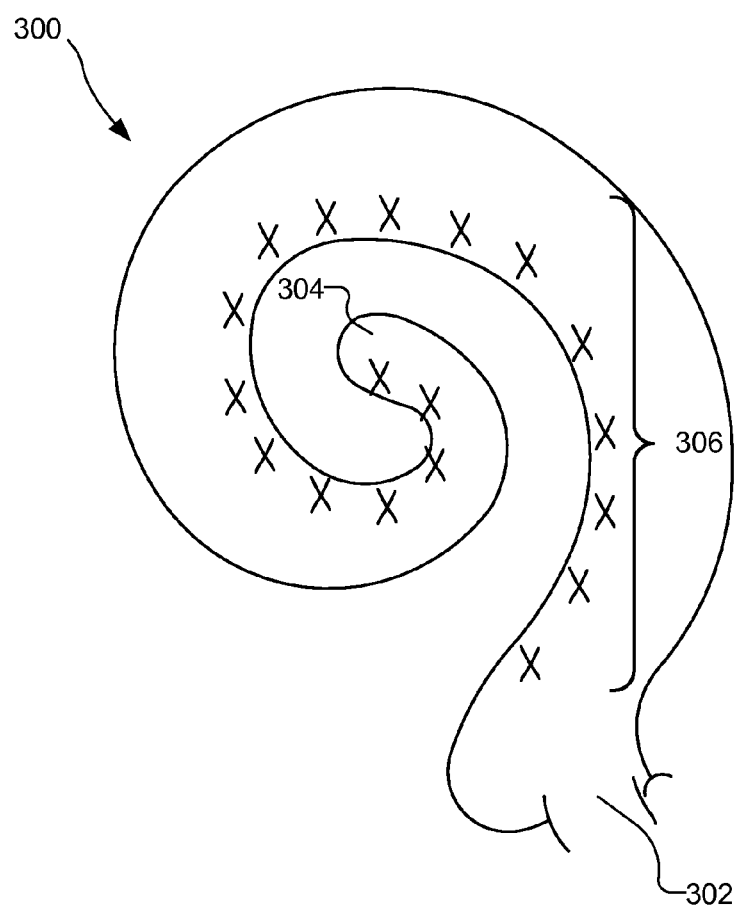
FIG. 1C illustrates a schematic structure of a typical human cochlea.

FIG. 10 schematically illustrates the structure of a human cochlea 300. As shown in FIG. 1C, the cochlea 300 is in the shape of a spiral beginning at a base 302 and ending at an apex 304. Within the cochlea 300 resides auditory nerve tissue 306, which is denoted by Xs in FIG. 10. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency. A cochlear prosthesis may therefore be implanted within a patient with sensorineural hearing loss and configured to apply electrical stimulation to different locations within the cochlea 300 to provide the sensation of hearing. For example, the electrode lead 114 may be disposed within the cochlea 300 such that electrodes 112 are in communication with auditory nerve tissue 306 within the cochlea 300. Electrical stimulation may then be selectively applied through electrodes 112 to the auditory nerve tissue 306.

In some cochlear implant systems, sound processor 106 and microphone 108 are located external to the patient while cochlear stimulator 110 is located internal to (i.e., implanted within) the patient. To facilitate communication between sound processor 106 and cochlear stimulator 110, telemetry circuitry may be included within sound processor 106 and cochlear stimulator 110. Such telemetry circuitry disadvantageously requires relatively large amounts of operating power, as previously discussed.

To reduce the amount of operating power required to facilitate cochlear stimulation, various percutaneous cochlear implant systems will be described herein that provide for direct (e.g., wired) connection between sound processor 106 and cochlear stimulator 110. In this manner, as will be described in more detail below, operating power may be minimized, telemetry components may be reduced and/or eliminated, and the overall size and weight of components used for cochlear stimulation may be reduced.

II. Exemplary Percutaneous Port

As used herein, the term "percutaneous port" (or "percu-port", for short) refers to a means for making electrical and/or signal connection through the skin of a patient, e.g., from an external component or device to an implanted device or component, or vice versa, without the need for transmitting an RF signal or using inductive coupling schemes. In its simplest form, one could argue that a "percutaneous port" is simply a wire that passes through the skin. However, a wire that just passes through the skin would not function for purposes of the present disclosed subject matter because infection would occur within a short time, and the wire would have to be removed. Hence, a "percutaneous port" of the type used with the systems described herein not only must provide the direct electrical or signal connection that a wire, or wires, passing through the skin would provide, but it must do so in a way that greatly minimizes or eliminates the risk of infection. An exemplary percutaneous port of the type that may be used with the invention(s) described herein is more fully described in applicants' (Mann and He) copending U.S. patent application Ser. No. 12/390,425, filed Feb. 21, 2009, entitled "Partially Implantable Medical Devices and Methods", which application is incorporated herein by reference.

Figure 2A:
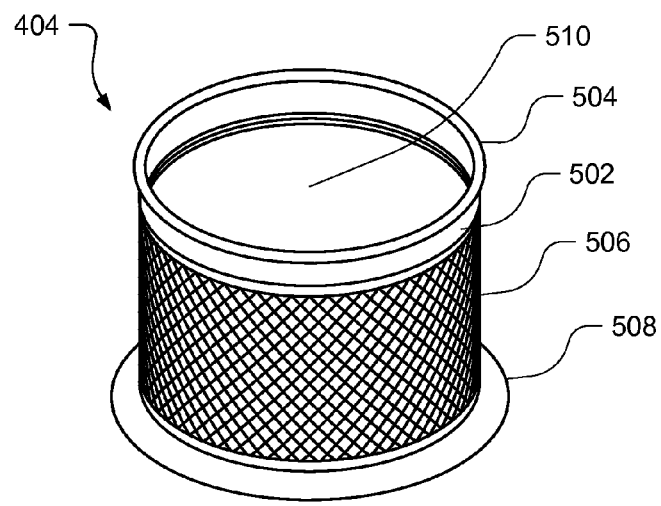
FIG. 2A illustrates an exemplary percutaneous port of the type that may be used in connection with the systems and methods described herein.

FIG. 2A is a perspective view of an exemplary percuport 404 that may be used in connection with the systems and methods described herein. It will be recognized that the port 404 shown in FIG. 2A is merely illustrative of the many different types of ports that may be used in connection with the systems and methods described herein. FIG. 2C shows a sectional view of the port 404 when embedded in skin tissue so that its base resides against the skull of a patient.

Figure 2B:
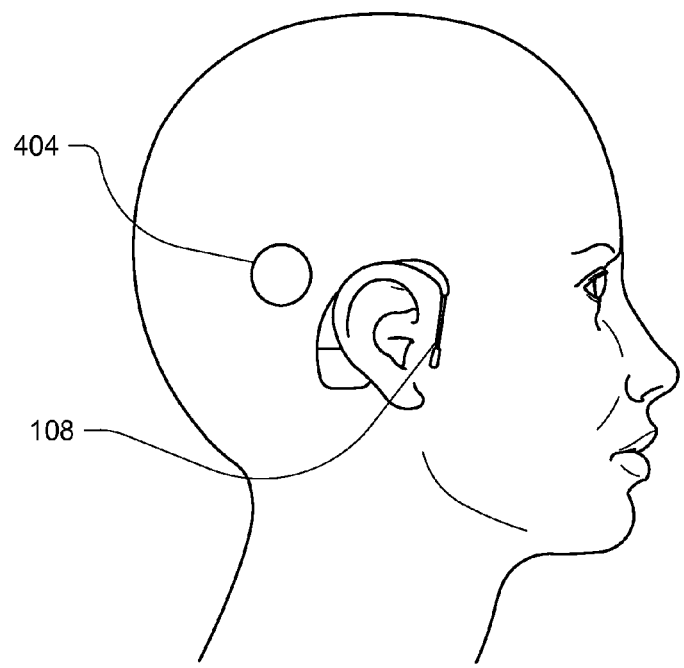
FIG. 2B illustrates a representative implant location of a percutaneous port used in connection with the systems and methods described herein.
Figure 2C:
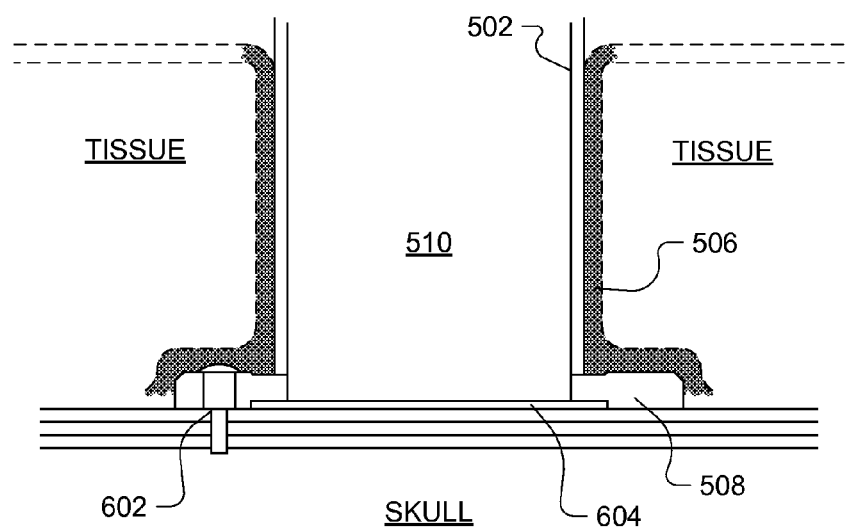
FIG. 2C is a cross-sectional view of the percutaneous port of FIG. 2A when placed through the skin of a patient so as to reside against the skull of the patient.

FIG. 2B illustrates an exemplary implant location of percutaneous port 404 on the head of a user of a percutaneous cochlear implant system. As shown in FIG. 2B, port 404 will typically be located a certain distance behind the ear (e.g., 2-3 cm) and behind the hair line. Such an implant location is advantageous for many reasons. For example, because port 404 is located behind the hairline, it is generally not visible or noticeable to others because it is just a small circle near the skin surface, much like a mole or scab. In some examples, this circle may be colored or otherwise disguised. Advantageously, such a configuration eliminates the need for a processor worn on or behind the ear (BTE), a headpiece, and a cable. Such parts or components of a typical cochlear implant system, i.e., a cable, headpiece, and BTE processor, are generally cosmetically disliked by many users. Moreover, such components—worn on the head or ear or dangling therefrom—may also cause maintenance and/or reliability problems.

As illustrated in FIG. 2B, microphone 108 may be inserted into the ear canal, which is the ideal location for a microphone to be placed because the natural sound collecting features of the pina of the human ear direct sound waves into the ear canal. In this manner, microphone 108 may be less noticeable or even completely hidden. Such microphone may be electrically coupled to a sound processor inserted into the port 404, or housed within a lower partition of the port 404, or implanted in an hermetic housing positioned near the location of port 404, by wires within an implanted cable. Alternatively, the microphone 108 may communicate wirelessly with a sound processor associated with the percutaneous cochlear implant system, as is known in the art.

Microphone 108 may also be located at other locations within the ear or on the head of the user, as suits the need(s) a particular user. For example, the microphone may be placed at the end of a boom supported by a hook worn on the ear so as to be positioned near the opening of the ear canal, much like the T-Mic® microphone manufactured by Advanced Bionics of Valencia Calif. See, e.g., U.S. Pat. Nos. 6,775,389; 7,003,876; 7,167,572, incorporated herein by reference.

The exemplary port 404 shown in FIGS. 2A and 2C is circular in cross-section in order to accommodate one or more circular components. It should be noted, however, that port 404 may have cross-sectional shapes other than circular in order to, for example, accommodate components that are oval, square, rectangular, or otherwise shaped.

Port 404 may have any suitable length as may serve a particular patient or application. In some examples, the length of port 404 may be slightly more than the thickness of the skin, which may be only a few millimeters (mm) thick in an infant or 8 to 10 millimeters (mm) in some patients. As needed, a pocket having a depth of a few millimeters may be made in the skull or a spacer can be added in order to accommodate a port 404 having a depth greater than the depth of the skin above the skull. In some examples, a proximal end of port 404 may extend beyond the skin when implanted by up to 2 mm. Alternatively, the proximal end of port 404 may be substantially flush with the surface of the skin. Hence, an exemplary length of port 404 may be 12 to 14 mm. In other patients (e.g., children) with skin that is less thick (e.g., 5 mm), the length of port 404 may be reduced accordingly. For example, the length of port 404 may be 6 to 7 mm for such patients. Likewise, the diameter of port 404 may vary as may serve a particular patient. It will be recognized that these measurements, and all others presented herein and in the drawings, are merely illustrative and are not to be construed as limiting in any way.

As shown in FIGS. 2A and/or 2C, port 404 may include a tubular wall 502 with a rounded rim 504, a layer of porous material 506 surrounding wall 502, and a base flange 508. Rounded rim 504, which may be located adjacent to the epidermal surface when port 404 is implanted into the patient, strengthens tubular wall 502 and eliminates what might otherwise be a sharp edge that may be uncomfortable to the touch. Tubular wall 502 defines a tubular or cylindrically shaped lumen or cavity 510 in which one or more components of a percutaneous cochlear implant system 400 may be housed and/or through which one or more components may be accessed and/or controlled. (The cavity 510 may be made to have cross-sectional shapes other than tubular or cylindrical, e.g., oval, rectangular, square, or triangular, although any corners associated with polygonal shapes are typically rounded sufficiently to avoid sharp or uncomfortable edges). Tubular wall 502 may be made out of any suitable biocompatible material (e.g., titanium, nitinol, stainless steel, gold, or platinum) as may serve a particular application.

In some embodiments, a center protrusion may extend up from the bottom or floor of the port 404 to accommodate rotation or keyed-positioning of components that are inserted into the cavity 510 of the port 404, as is explained in more detail hereinafter.

The layer of porous material 506, which may at a minimum be located just below the patient's epidermis and in contact with the dermis, is configured to encourage tissue ingrowth and vascularization so as to create an infection resistant barrier around tubular wall 502 after implantation. The layer of porous material 506 extends around the entire circumference of tubular wall 502 (as shown) and may extend from one longitudinal end of tubular wall 502 to the other, or over only a portion of tubular wall 502. In certain exemplary implementations, the layer of porous material 506 may include a mesh of intersecting fibers of any suitable biocompatible material, such as a biocompatible metal (e.g., titanium, nitinol, stainless steel, gold, or platinum) or a biocompatible polymeric material (e.g., polyolefins, Teflon, nylon, Dacron, or silicone). The mesh may be formed by cross-winding the fibers in multiple layers to define a porosity conducive to promoting tissue ingrowth (e.g., pore sizes within a range of 50 to 200 microns and having a porosity of 60 to 95%). The infection resistant barrier may be enhanced by incorporating antimicrobial and/or anti-inflammatory constituents into or beyond the layer of porous material 506. Additional details concerning such porous material layers may be found in U.S. Patent Pub. Nos. 2004/0204686, 2007/0112334 and 2007/0149949, each of which is incorporated herein by reference.

Base flange 508 may be configured to facilitate fixation of port 404 to the skull. To this end, one or more screws 602, or other affixation devices, may be used to affix base flange 508 of port 404 to the skull. In some alternative embodiments, port 404 is not affixed to the skull and instead simply floats with the tissue ingrowth that forms into porous material 506 to secure port 404 within the tissue.

As shown in 2C, a feedthrough plate 604 is disposed at a distal end of lumen 510 so as to be in contact with tubular wall 502. Together with tubular wall 502, feedthrough plate 604 defines a receiving region or cavity 510 into which one or more components may be inserted. In some embodiments, feedthrough plate 604 comprises a bottom surface of port 404. In other embodiments, feedthrough plate 604 comprises one wall of an hermetic chamber built into the port 404.

Feedthrough plate 604 may assume various shapes and forms. Whatever the shape or form, however, the function of the plate 604 is essentially the same: to provide a surface through which feed-through pins ("feedthrus") may extend in order to provide electrical conduction between one side of the plate to the other. This is necessary because one side of the plate defines a cavity or surface area that is appropriately sealed or protected from the surrounding environment, while the other side of the plate is not. Electrical circuitry that is implanted, for example, must typically reside in an hermetically sealed cavity or otherwise be sealed and protected from body fluids and tissue, if it is to reliably perform its intended function over a long period of time.

III. Exemplary Cochlear Implant Systems utilizing a Percutaneous Port

Figure 3:
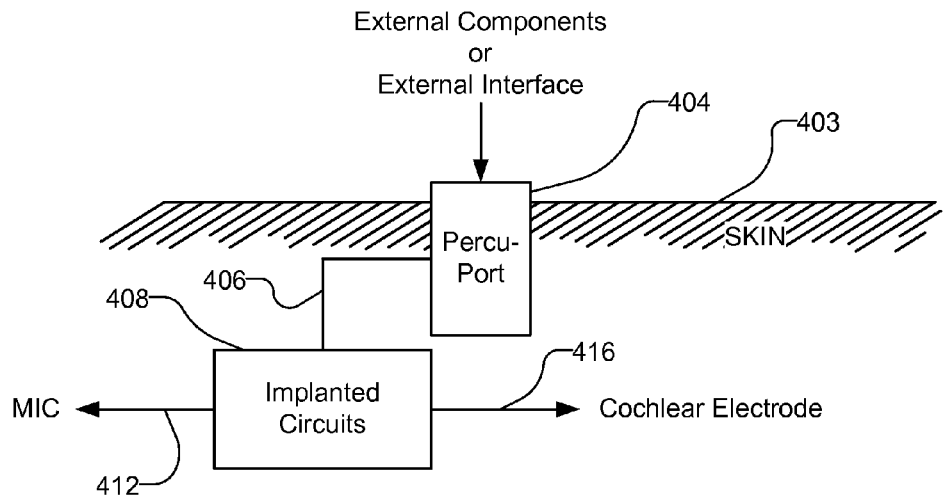
FIG. 3 schematically depicts the manner in which a percutaneous port is used with the systems and methods described herein to provide a link between external and implanted components of the percutaneous cochlear implant system (PCIS).

A percutaneous port 404 is found in all embodiments of the systems and methods described herein relating to percutaneous cochlear implant systems (PCIS). Thus, as seen in FIG. 3, every PCIS includes a percuport 404 that is embedded in the skin 403 of a patient. Below the skin, or "implanted" in the patient, are implanted circuits 408 that carry out the functions of the PCIS. These functions are the same as are carried out in any cochlear implant system, described previously in connection with FIGS. 1A, 1B and 10. The circuits 408 have leads 412 and 416 extending therefrom that connect respectively to a suitable microphone ("MIC"), e.g., an in-the-canal (ITC) microphone, and a cochlear lead with electrodes. The circuits in housing 408 are connected to the percuport 404 via a suitable connection 406, which may be a flexible cable. Alternatively, as illustrated below in connection with FIG. 5, such connection may be a direct connection where the percuport 404 is affixed to the top or side of the circuitry housing 408.

It is noted here that as various embodiments and/or details associated with one or more implant configurations of a PCIS are described hereinafter, the particular electronic circuitry that is housed in a particular module of a particular configuration, including its manner of operation, programming codes, stimulation levels and stimulation patterns, and the like, will not be described in detail, if at all. This is because such details are generally not the subject of the present application and the invention(s) described and claimed herein. Rather, the invention(s) described and claimed herein focus more on the manner in which the particular modules used by or within a particular configuration of a PCIS can be configured or arranged relative to a percutaneous port 404. Thus, it is seen that a percutaneous port 404 is a common feature of all of these configurations.

The actual circuitry used within the various modules associated with the configurations of the PCIS of the present invention(s), as well as the assembly and manufacturing techniques used to make the implantable housings, leads, connectors and electrodes associated with these configurations, may be of any suitable design, whether presently existing or yet to be developed. In fact, that is one of the potential advantages of the present invention (in some configurations): by using circuits and components that already exist, and that have been tried and tested and approved for use in medical implantable devices, the percutaneous cochlear implant system(s) described herein may be brought to market much quicker than could otherwise occur.

Of course, as with any new configuration, some changes or revisions in existing designs and circuits need to be made in order to have all the modules, circuits and components of the invention interface and cooperate together for the system to function correctly and efficiently. Where such changes are more than routine, and not readily discernable by a person of skill in the art given the descriptions and explanations already provided herein, such will be described, as necessary, with sufficient detail to allow a person of skill in the art to make and practice those revisions and changes.

Figure 4:
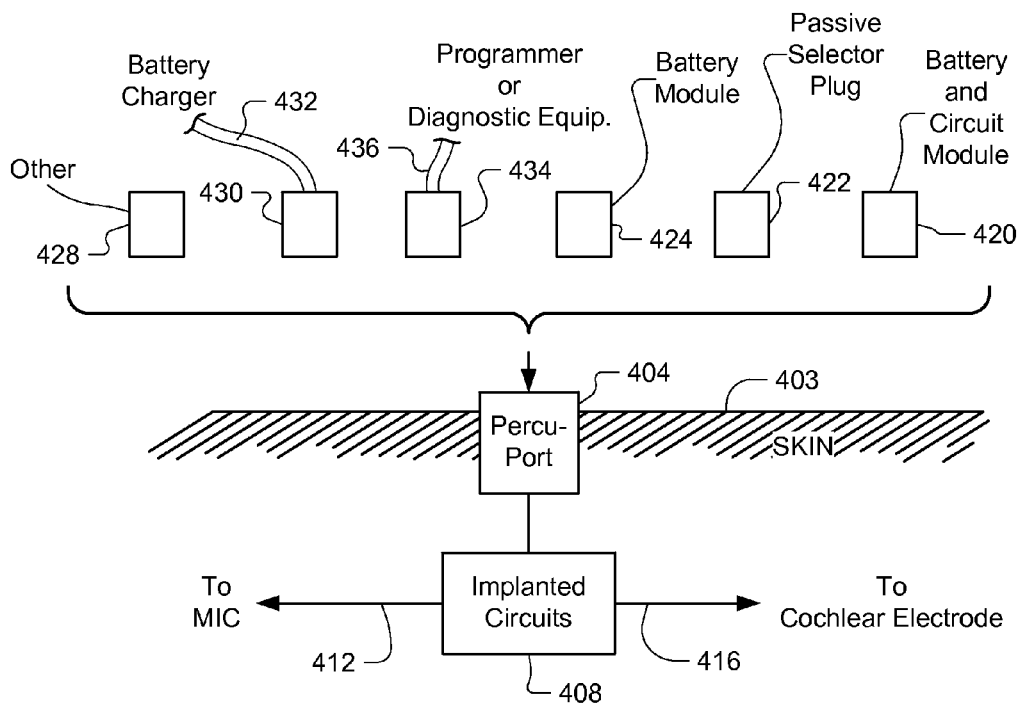
FIG. 4 schematically depicts, in an exploded view, exemplary components of a PCIS, or elements used with a PCIS, that may reside external to the percutaneous port, any one of which may be selectively inserted into the percutaneous port in order to provide a desired function.

As seen in FIG. 3, various elements or components of a PCIS that are external to the patient, i.e., not implanted under the skin, may interface with the implanted circuits 408. FIG. 4, for example, shows, in an exploded view, exemplary devices and components that may interface with the implanted circuits 408. The particular external devices and components which are used depend on the particular PCIS design that is used for the implanted circuits 408.

For example, one component that may interface with the implanted circuits 408 through the percuport 404 is a battery/circuit module 420. Such module includes a battery, which provides operating power for both the implanted and external components of the PCIS. Such module also includes at least some circuitry, e.g., front-end sound processing circuitry, used with the PCIS. While FIG. 4 shows the battery and circuit module 420 as one module, it is to be understood that these components could be realized in separate modules or components that are placed piggy-back into the percuport 404. That is, a speech processor module could be inserted into the most distal end of the percuport 404, and then a battery, e.g., a disc battery, could be inserted in the proximal end of the percuport so as to reside on top of the speech processor module. The advantage of having both the battery and speech processing circuits located or housed in the percuport 404 is that they can be readily replaced and upgraded, or recharged, as needed.

Alternatively, if the implanted circuits 408 include all of the circuitry necessary to carry out the sound processor and cochlear stimulator functions, but not a battery, then a battery module 424, which in its simplest form is just a battery, e.g., a disc battery, may be all that is needed to be inserted into the percuport 404.

Other modules, represented by the generic box 428 in FIG. 4, may also be fabricated for insertion into the percuport 404 in order to add functionality to the PCIS. Module 428, for example, could be an FM receiver adapted to receive a FM signal that, once received within the module 428, can be sent to the implanted circuits 408, thereby enabling the user of the PCIS system to hear whatever FM signal is received by the module 428.

In a similar manner, module 428 could be a Bluetooth® receiver that enables reception of signals that are transmitted to or from a mobile phone or other device that utilizes Bluetooth® technology. Alternatively, module 428 could include flash memory that stores prerecorded audio signals, such as MP3 files, that when inserted into the percuport 404 allows the user to listen to an audio book, music or other prerecorded audio files.

Another component that can be inserted into the percuport 404, in accordance with some embodiments of the PCIS described herein, is a passive selector plug 422. In this context, the term "passive" simply means that in this embodiment, there is no electronic circuitry included within the selector plug 422. Rather, the passive plug functions as a stopper, like a cork, that is inserted into the cavity of the percuport 404. Unlike a cork, however, the plug is adapted for rotational movement within the percuport 404, and includes some sensible elements, e.g., conductive metal contacts or traces, spaced around its distal end or sides in a desired pattern. Because of this rotational movement, and the pattern of conductive traces or contacts included on at least one surface thereof, this passive selector plug is also referred to herein as a "cartridge".

The passive selector plug 422 will be described in more detail hereinafter. Essentially, however, the passive selector plug 422, when inserted into the port 404, allows the user, by manually rotating the plug in prescribed directions (clockwise, counterclockwise), and prescribed distances or magnitudes (¼ turn, ⅓ turn, ½ turn, etc.) to manually control some functions of the PCIS, such as on/off, volume, sensitivity and the like.

For many embodiments of the PCIS described herein, there will be a recurring need to access the implanted circuits 408 for the purpose of charging the battery (if a rechargeable battery is included in the implanted circuits 408) and for programming the circuits or performing diagnostic tests on the circuits. Battery charging is readily achieved by simply inserting a battery charger plug 430 into the percuport 404. Such battery charger plug 430 is connected to a cable 432 that in turn connects to an appropriate external battery charger circuit. Alternatively the battery charger can be a small module that includes a battery that is connected to a plug that fits into the percuport 404. Also, an auxiliary battery can be inserted into the percuport 404 to extend the operating time of a system with an implanted rechargeable battery.

Programming is similarly achieved by inserting a programming plug 434 into the percutaneous port 404. A cable 436 attached to the plug 434 allows the implanted circuits 408, via the interface provided by the percuport 404, to be connected directly to external programming or diagnostic equipment. Such external programming or diagnostic equipment is typically realized with custom software loaded on a laptop or other suitable computer, as is known in the art.

Thus, it is seen that the PCIS system shown in FIGS. 3 and 4 allows a wide variety of PCIS configurations and embodiments to be realized. The percutaneous port 404 is the common element that makes all of these configurations and embodiments possible.

Figure 5:
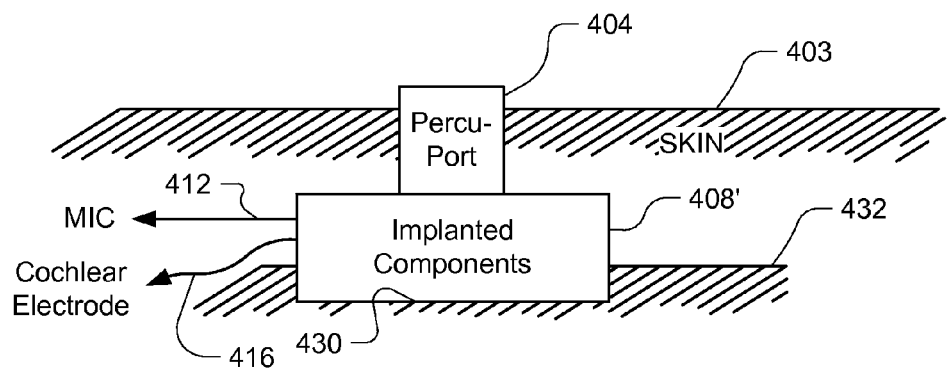
FIG. 5 schematically illustrates one representative embodiment of a PCIS wherein the implanted components reside below the percuport.
Figure 6:
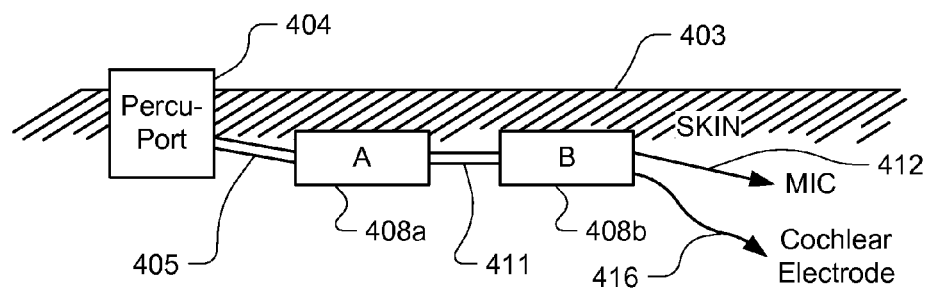
FIG. 6 schematically illustrates another representative embodiment of a PCIS wherein the implanted components reside in two or more implantable housings, labeled in FIG. 5 as housing "A" and housing "B", flexibly connected together.

Turning next to FIGS. 5 and 6, two specific embodiments of a PCIS are schematically illustrated that utilize the general principles illustrated in schematic block diagrams of FIGS. 3 and 4. In FIG. 5, for example, an embodiment of the invention is illustrated wherein all of the implanted components are housed in a single implanted housing 408' that is attached to the bottom of the percuport 404. The microphone cable 412 and the cochlear electrode cable 416, each of which connects to the circuitry in housing 408' via suitable feedthrus, exit at one side of the implanted circuits housing 408. A pocket 430, having a depth, e.g., of 2-3 mm, may be formed in the skull bone 432, as required, in order to provide a suitable surface with adequate depth for the PCIS.

FIG. 6 schematically illustrates an embodiment of the PCIS similar to the one shown in FIG. 5, except that two or more housings are used for the implanted circuitry 408. In FIG. 6, two housings, labeled "A" and "B" are used. A first housing, 408a, for example, is flexibly connected to the percuport 404 via a flexible cable 405. This first housing houses, e.g., a battery and the sound processing circuitry. A second housing, 408b, flexibly connected to the first housing 408a via a suitable flex cable 411, houses the cochlear stimulator circuitry. Lead 412 connects to an ITC (in-the-canal) microphone, or other implanted microphone; and lead 416 connects to the cochlear electrode. Because the two housings are flexibly connected to each other, and to the percuport 404, they can more easily conform to the curvature of the skull.

Figure 7:
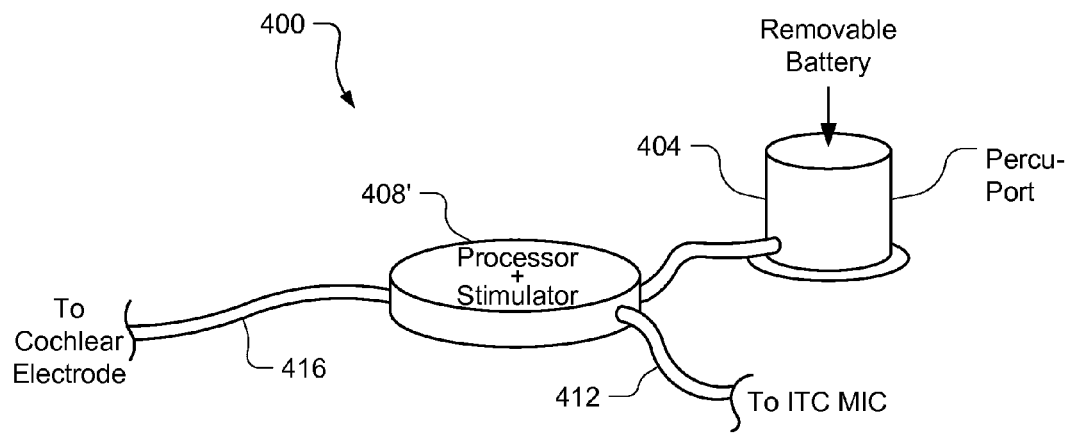
FIG. 7 illustrates a perspective view of a representative embodiment of a PCIS wherein all of the circuitry of the PCIS is implanted except for a battery, and wherein the battery is removably housed inside the percuport.

Turning next to FIG. 7, a perspective view of a PCIS 400 is depicted that includes a percuport 404 adapted to have a battery module 424 (see FIG. 4) removably inserted therein. The percuport 404 is connected to a single implantable housing 408' via flexible calbe 406. Sound processor and cochlear stimulator circuitry is housed in the housing 408'. A lead 412 connects to an ITC MIC. Another lead 416 connects to a cochlear electrode. The cochlear electrode may have any number of electrodes thereon, but a preferred number of cochlear electrodes is twelve to 32, but other numbers of electrodes can be used.

When the PCIS 400 needs to be programmed, the battery module placed in the percuport 404 may be removed and a programming plug 434 (see FIG. 4) may be inserted into the port 404 in its place. The programmer connected to the programming plug 434 provides operating power to the PCIS circuitry during the programming process. When the programming is completed, the programming plug 434 is removed, and is replaced by the battery module 424.

Figure 8:
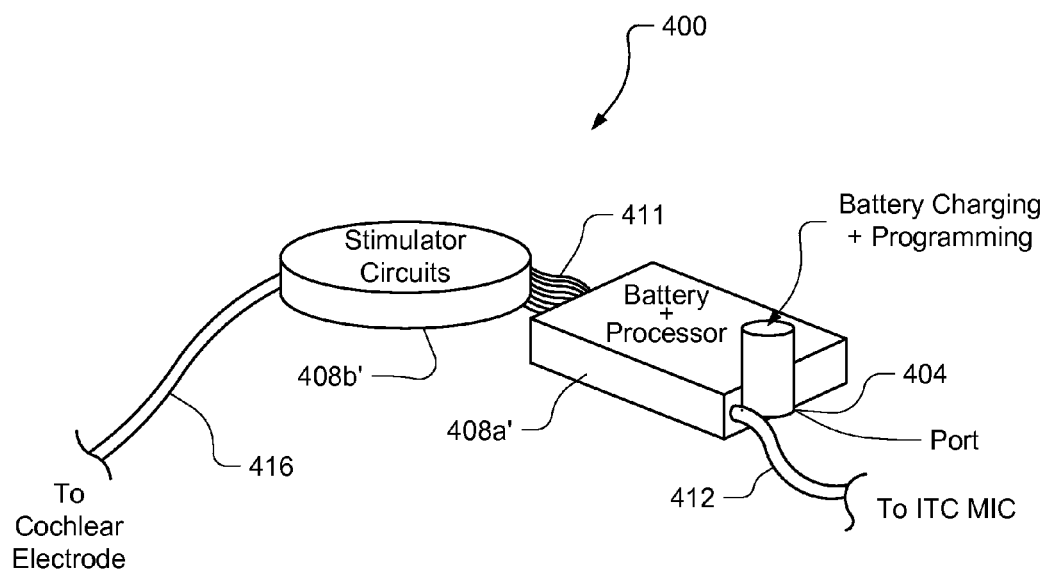
FIG. 8 illustrates a perspective view of another representative embodiment of a PCIS wherein all of the circuitry of the PCIS is implanted, including the battery, in two implanted housings that are flexibly connected together.

Next, with reference to FIG. 8, a perspective view of another embodiment of a PCIS 400 is illustrated. This embodiment, like the embodiment shown in the schematic diagram shown in FIG. 6, includes two implantable housings 408a' and 408b'. Housing 408a' includes a rechargeable battery and processor circuitry. Housing 408b' includes appropriate cochlear stimulation circuits. The two housings are interconnected with a flex cable 411.

Still with reference to FIG. 8, a percuport 404 attaches directly to a side of housing 408b'. A microphone lead 412 exits from a side of housing 408a' and connects to a suitable ITC (in-the-canal) microphone, or other microphone located elsewhere. A cochlear electrode lead 416 exits from a side of housing 408b' and connects to a cochlear electrode array at a distal end thereof.

Because housing 408a' includes a rechargeable battery, percuport 404 is used to perform battery charging and programming/diagnostic functions. When not recharging, or not programming, a passive selector plug 422 (see FIG. 4) may be inserted into the percuport 404. Such passive plug acts as a cover or seal to keep the percuport clean and free of dirt and other gunk that might otherwise accumulate there. Also, as described in more detail below, in accordance with one embodiment of the invention, the passive selector plug 422 may provide a means for allowing a user to manually select certain functions associated with operation of the PCIS, such as on/off, volume control and sensitivity control, simply by rotating the plug one direction or the other a prescribed amount in a prescribed sequence or pattern.

IV. Exemplary Percutaneous Cochlear Implant System (PCIS) Having all Operative Components Implanted Next with reference to FIGS. 9-25, one particular preferred embodiment of a PCIS made in accordance with the teachings and principles of the present invention(s) will be described in detail.

Figure 9:
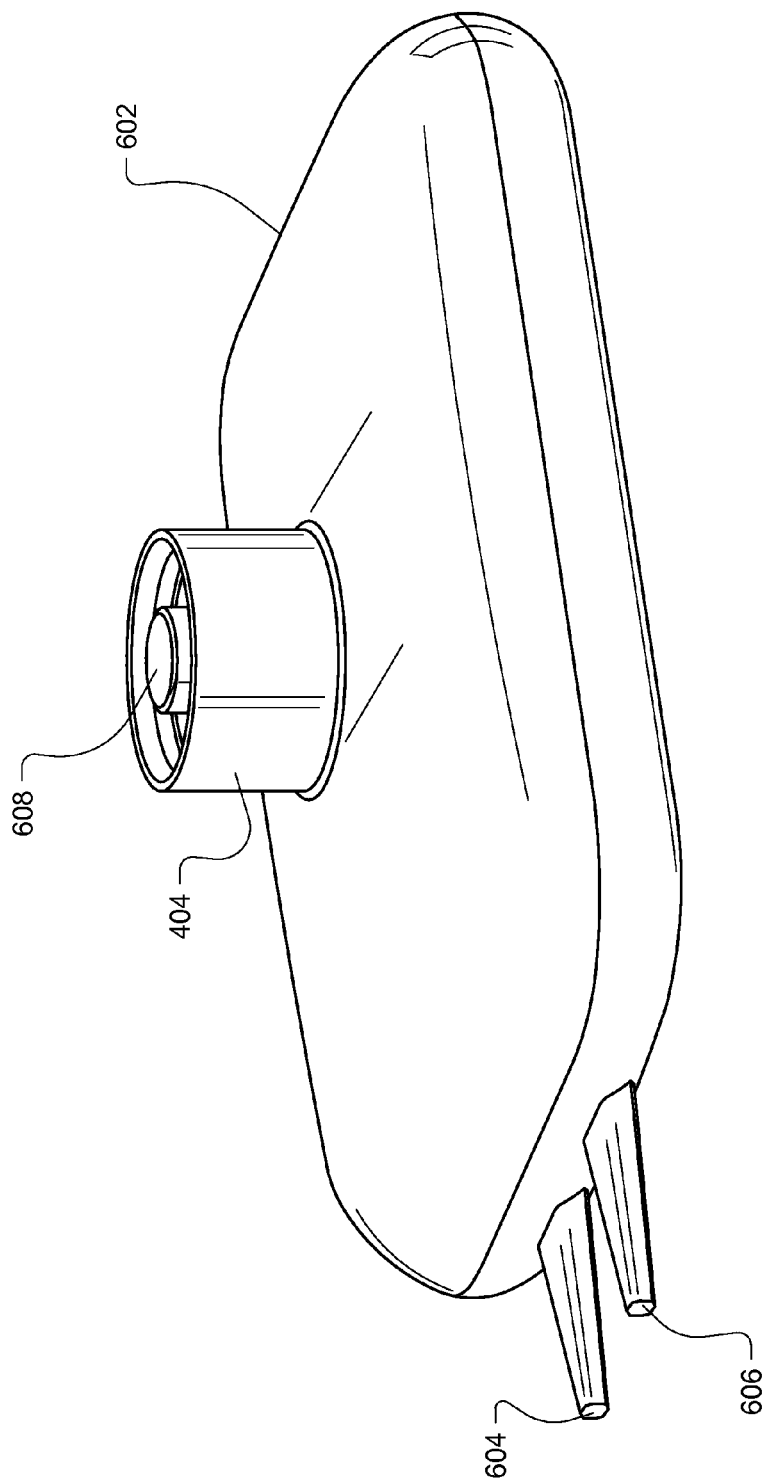
FIG. 9 shows a representative and preferred embodiment of a fully implantable PCIS wherein all of the circuitry of the PCIS is implanted in a single implanted housing that resides below the percutaneous port.

FIG. 9 shows a representative and preferred embodiment of a fully implantable PCIS 400 wherein all of the circuitry of the PCIS is implanted in a single implanted housing 602 that resides below a percutaneous port 404. That is, the percuport 404 is attached to, and integral with, an upper surface of the housing 602. It should be noted that a suitable mesh used to promote tissue ingrowth around the port 404 is not shown in FIG. 9, but is shown in subsequent figures.

The housing 602, percuport 404, including the mesh around the percuport 404 (not shown in FIG. 9) are made from a suitable biocompatible material, such as titanium. A first cable 604 exits from a side of the housing 602, as does a second cable 606. Strain relief for these cables is provided by silicon overmold. The cable 604 attaches to a suitable microphone (not shown in FIG. 9). The cable 606 attaches to a cochlear electrode lead (also not shown in FIG. 9).

The percuport 404 includes a protrusion 608 that extends upwards from a bottom surface of the port 404. Such protrusion may be used as a connector contact pin for a designated signal when a connector is plugged into the port 404. For example, the protrusion 608 may function as a ground pin, or it may function as a negative or positive voltage pin. Alternatively or conjunctively, in some embodiments, the protrusion 608 may function as a key using a slot so as to align a connector inserted into the port 404 with appropriate contacts therein. Also, in other embodiments, the protrusion 608 may be centered to facilitate rotation of a plug, or cartridge, within the port 404, to provide a manual user interface through rotation of the cartridge or plug a prescribed direction and amount.

Turning next to FIG. 10, there is shown, starting in the upper left hand corner and proceeding counter-clockwise: (a) an alternate perspective view of the fully implantable PCIS 400 of FIG. 9; (b) a side view of the PCIS 400; (c) a top view of the PCIS 400, showing the protrusion 608 with a slot incorporated so as to provide a keyed connection when connectors are inserted into the port 404; (d) a sectional view taken along the lines B-B of the PCIS 400; and (e) a sectional view taken along the lines A-A. of the PCIS 400. Also shown in FIG. 10 are representative dimensions associated with this particular preferred embodiment. Such dimensions are given in millimeters, and are not meant to be limiting, but only exemplary. As seen in FIG. 10, the overall length of the PCIS 400 is about 36 mm, the width is about 25 mm, and the height is about 11 mm.

Figure 11:
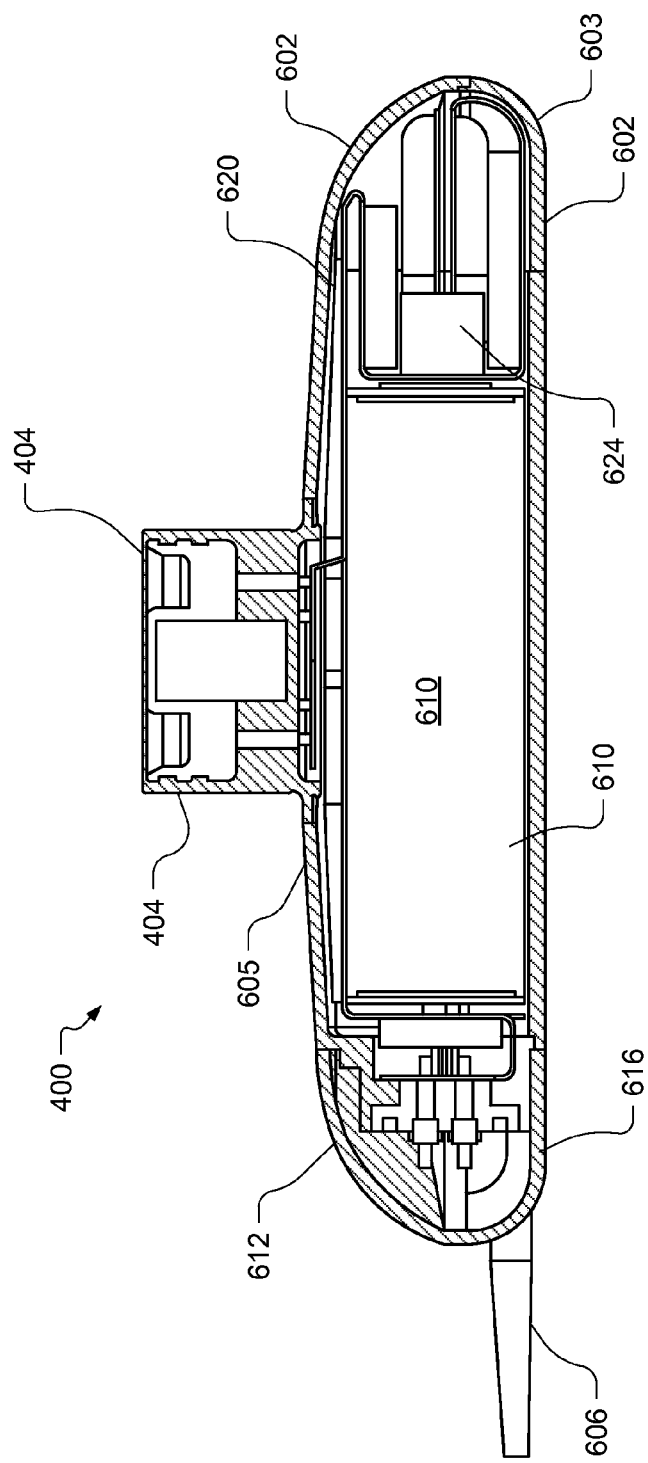
FIG. 11 is more detailed cross-sectional view of the fully implantable cochlear implant system shown in FIG. 10 taken along the lines A-A.

FIG. 11 is more detailed cross-sectional view of the fully implantable cochlear implant system 400 shown in FIG. 10 taken along the lines A-A. As seen in FIG. 11, the PCIS 400 is housed in a hermetically sealed housing or case 602. The case 602 is divided into two halves: a bottom or first half 603, and a top or second half 605. The top half 605 may also be referred to as a cover 605. A rechargeable battery 610 is housed in the center of the case 603. A feed through array 616 provides an array of feedthrus to which the cochlear electrode lead 606 and a microphone lead 604 may attach. The feedthrus are connected externally to the electrode lead 606 and the microphone lead 604 and then are potted with an insulating material 612 such as epoxy or silicone rubber to protect the exposed surface (i.e., the side of the array not within the hermetically sealed housing 602). Most of the electronic circuitry housed within the case 602 resides within the right side of the housing as it is oriented and shown in FIG. 11, although some of this circuitry also resides at other locations within the case, as will be evident from the description that follows. Advantageously, the circuit components mount on a flexible printed circuit board (PCB) 620 that is folded and arranged within the case 602 so as to take maximum advantage of the available space within the case or housing 602. Epoxy or other suitable encapsulant 624 fills voids and secures the circuit components in their desired locations within the housing 602. All of the circuitry needed for the PCIS to perform its desired cochlear implant function, including sound processing circuitry and cochlear stimulation circuitry, is housed within the same housing 602.

Figure 12:
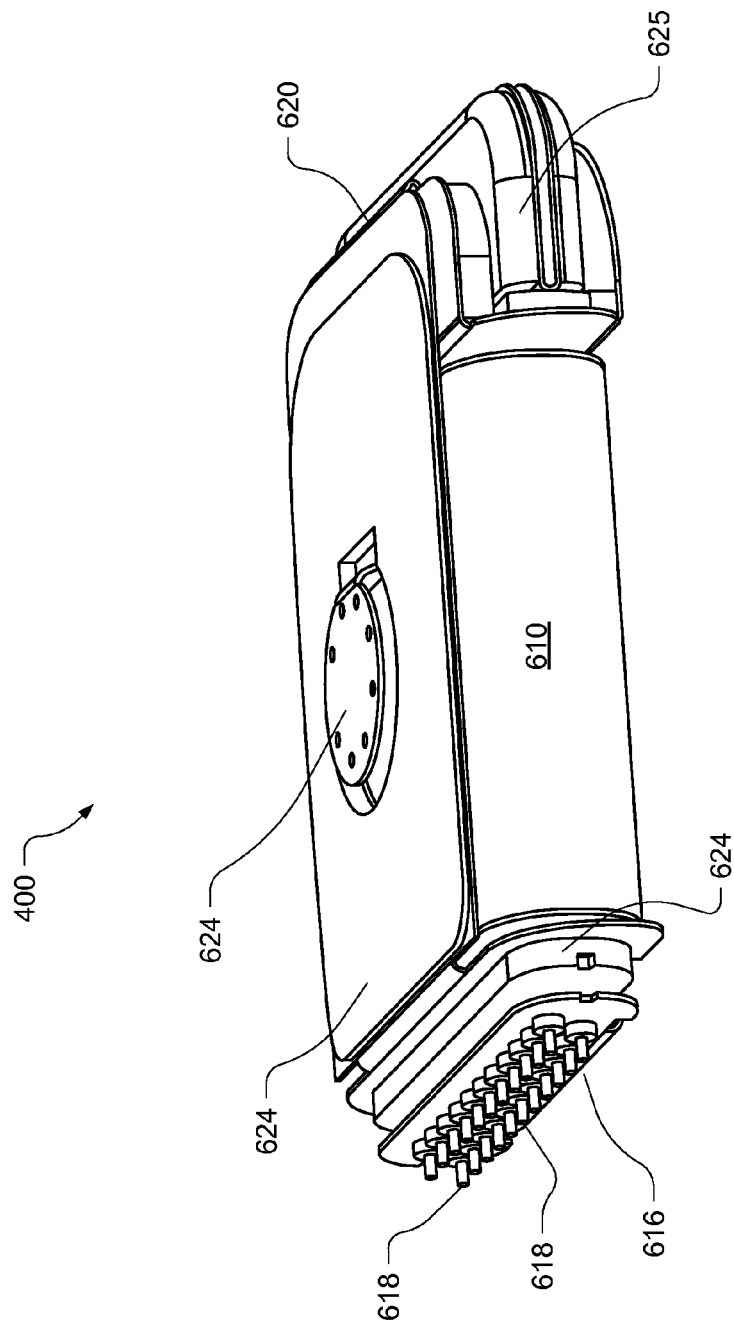
FIG. 12 is an isometric ("ISO") view of the PCIS shown in FIG. 10 with the covers and case removed.

Next, with respect to FIG. 12, there is depicted an isometric ("ISO") view of the PCIS 400 shown in FIG. 10 with the cover 605 and insulating material 612 removed, and with the case 602 removed. The encapsulant 624 can be seen in FIG. 12 as it covers and protects and fills in voids between all of the circuit components mounted on the flexible PCB 620. The feed-through array 616 provides an array, for this particular embodiment, of twenty-two 22 feed-through pins. In this embodiment, for example, sixteen or seventeen of these pins 618 may be used to provide electrical connection to the electrode array at the end of the electrode lead 606; while 4 or 5 of the pins 618 may be used to connect to the microphone cable 604. Others of the remaining pins may be used as redundant pins for key signal connections. The battery 610 is positioned in between the feed-through array 616 and most of the circuitry mounted to the flexible PCB 620. An additional flex circuit 624 is provided above the battery 610 for electrically mating with the port connector 404 (not shown in FIG. 12).

FIG. 13 shows an ISO (top) and side (bottom) view of the PCIS 400 shown in FIG. 10 with the cover 605, insulating material 612, case 602, battery 610 and feed-through pins 618 removed, and further shows the manner in which a folded flex printed circuit board (PCB) 620 fits over and around the location where the battery is placed.

Figure 14A:
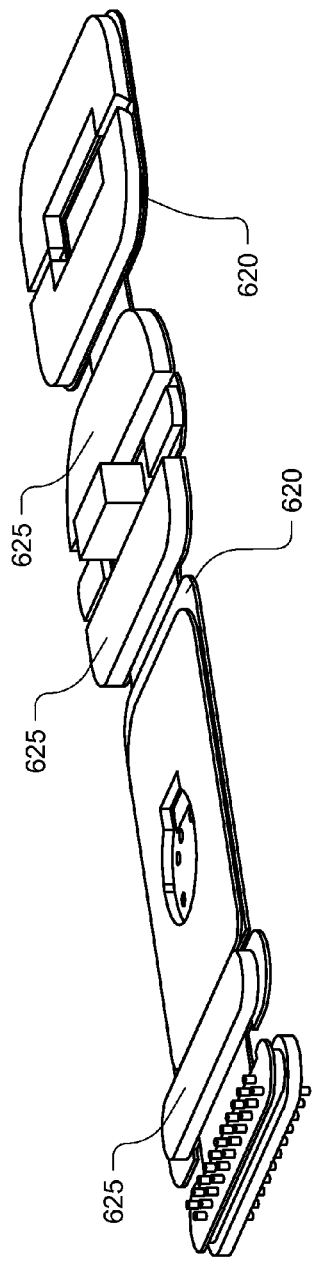
FIG. 14 shows an ISO view (FIG. 14A) and side (FIG. 14B) view of the flex PCB of FIG. 13, with the flex PCB placed flat for component assembly. The side view (FIG. 14B) also shows, for reference purposes, the battery.
Figure 14B:
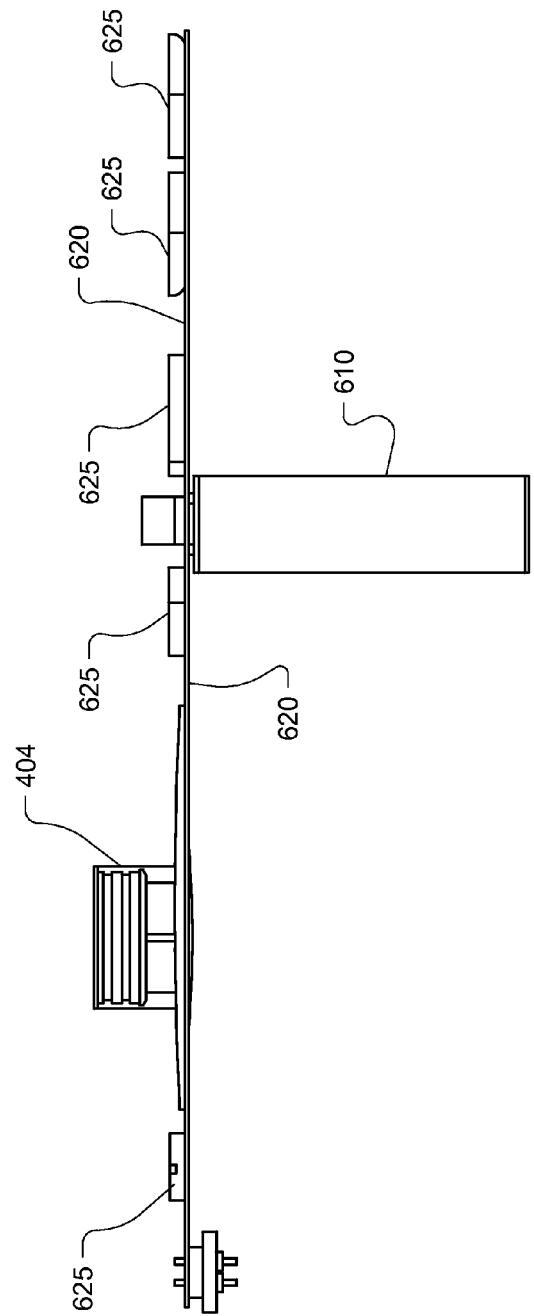

FIG. 14 shows an ISO (top) and side (bottom) view of the flex PCB 620 of FIG. 13, but with the flex PCB 620 placed flat for component assembly. The side view (bottom) also shows, for reference purposes, the battery 610 and the port connector 440. The components mounted on the PCB 620 are molded over with epoxy blocks 625.

Figure 15:
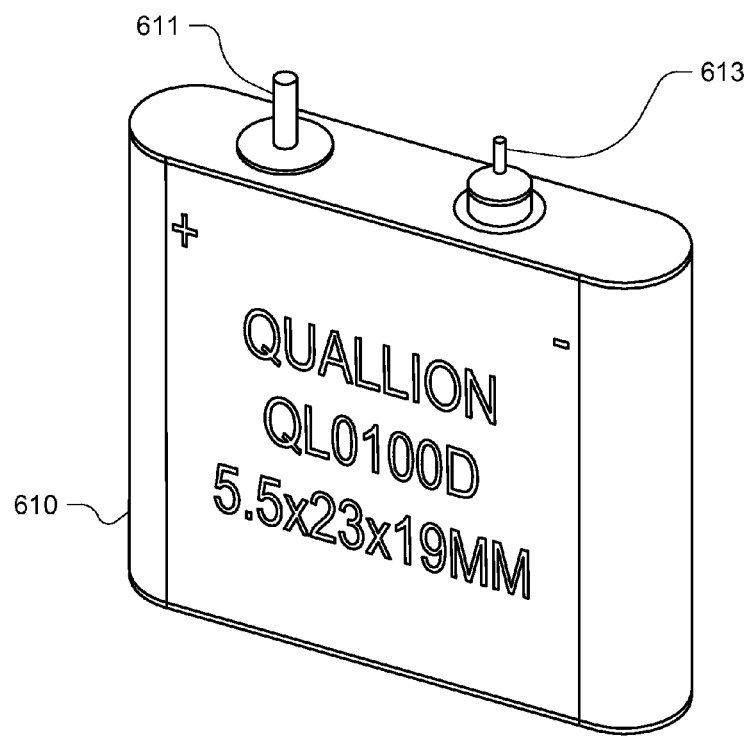
FIG. 15 illustrates a preferred battery that may be used with the fully implantable PCIS shown in FIGS. 9-11.

Next, with reference to FIG. 15, there is shown a preferred lithium ion rechargeable battery 610 that may be used with the fully implantable PCIS 400 shown in FIGS. 9-11. The battery comprises a 100 mAh battery. It has dimensions of approximately 5.5×23×19 mm. It is commercially available from Quallion Corporation, of Sylmar, Calif., as Part No. QL0100D. A positive terminal 611 and a negative terminal 613 are located at one end of the battery.

Figure 16:
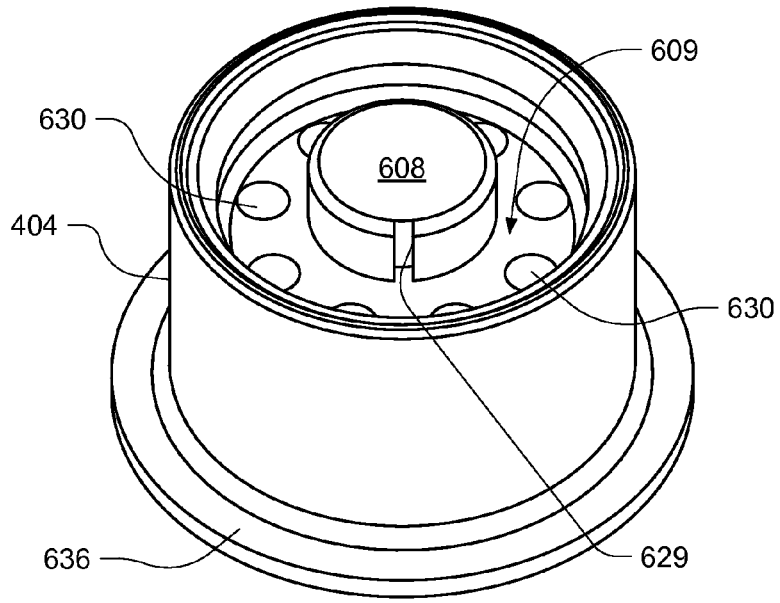
FIG. 16 depicts an ISO view of one embodiment of a percutaneous port that may be used with the PCIS shown in FIGS. 9-11 as viewed from a location above the percuport, and thus depicts a view of the interior of the percuport.

FIG. 16 depicts an ISO view of one embodiment of a percutaneous port connector 404 that may be used with the PCIS 400 shown in FIGS. 9-11 as viewed from a location above the percuport, and thus depicts a view of the interior of the cavity 609 within the percuport 440 where a mating connector may be inserted. An array of eight contacts 630 are spaced around the periphery of the bottom on the cavity 609. The center post is slotted with a slot 629 to enable a keyed connection when a plug, as a mating connector, is inserted into the percuport and must maintain a known relationship relative to the contacts when so inserted.

Figure 17:
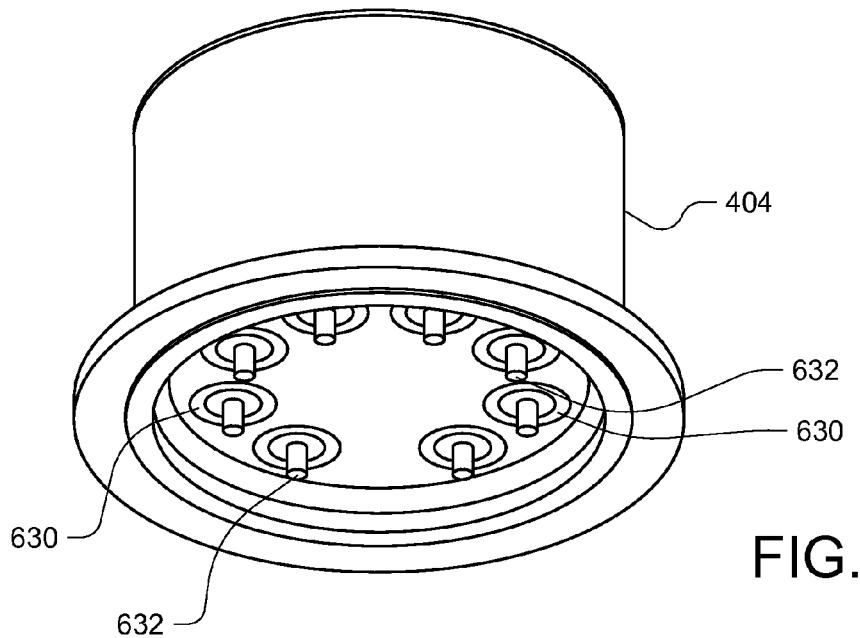
FIG. 17 depicts an ISO view of the percutaneous port of FIG. 16 as viewed from a location below the percuport, and thus depicts a view of the underneath side of the percuport.

FIG. 17 depicts an ISO view of the percutaneous port 440 of FIG. 16 as viewed from a location below the percuport 440, and thus depicts a view of the underneath side of the percuport. As seen from this underneath side, terminal pins 632 extend downward so as to make electrical contact with the flex PCB 620. A flange 636 around the bottom of the percuport 440 provides a surface that can be welded to the surface of the PCIS housing 602.

Figure 18:
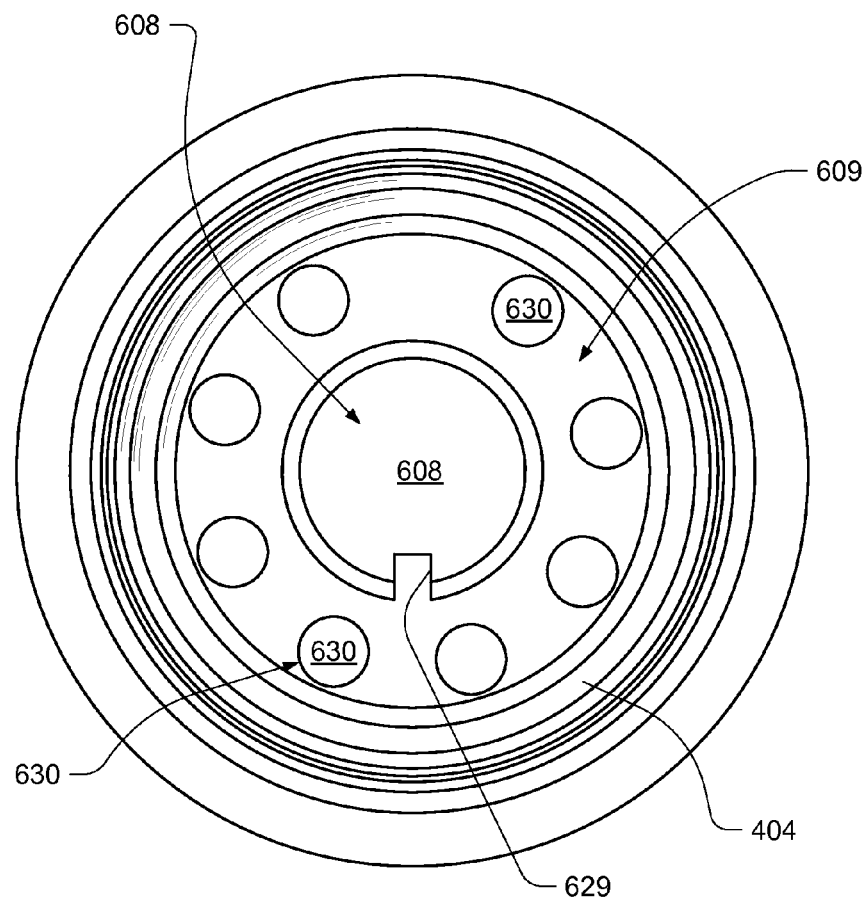
FIG. 18 depicts a top view of the percutaneous port of FIG. 16, and illustrates the manner, in accordance with this embodiment of the percuport, that the center protrusion includes a slot to provide a keyed connection.

FIG. 18 depicts a top view of the percutaneous port 404 of FIG. 16, and illustrates the manner, in accordance with this particular embodiment of the percuport connector 404, that the center protrusion 620 incorporates a slot 629 to provide a keyed connection with the eight contacts 630. In some embodiments of the percuport 404, described hereinafter, the mating plug or cartridge inserted into the cavity 609 can be manually rotated about the axis of the protrusion 620 in order to provide a user interface that allows a user or medical personal to generate control signals, as needed, by rotating the plug or cartridge a prescribed direction and distance within a prescribed time period.

Figure 19:
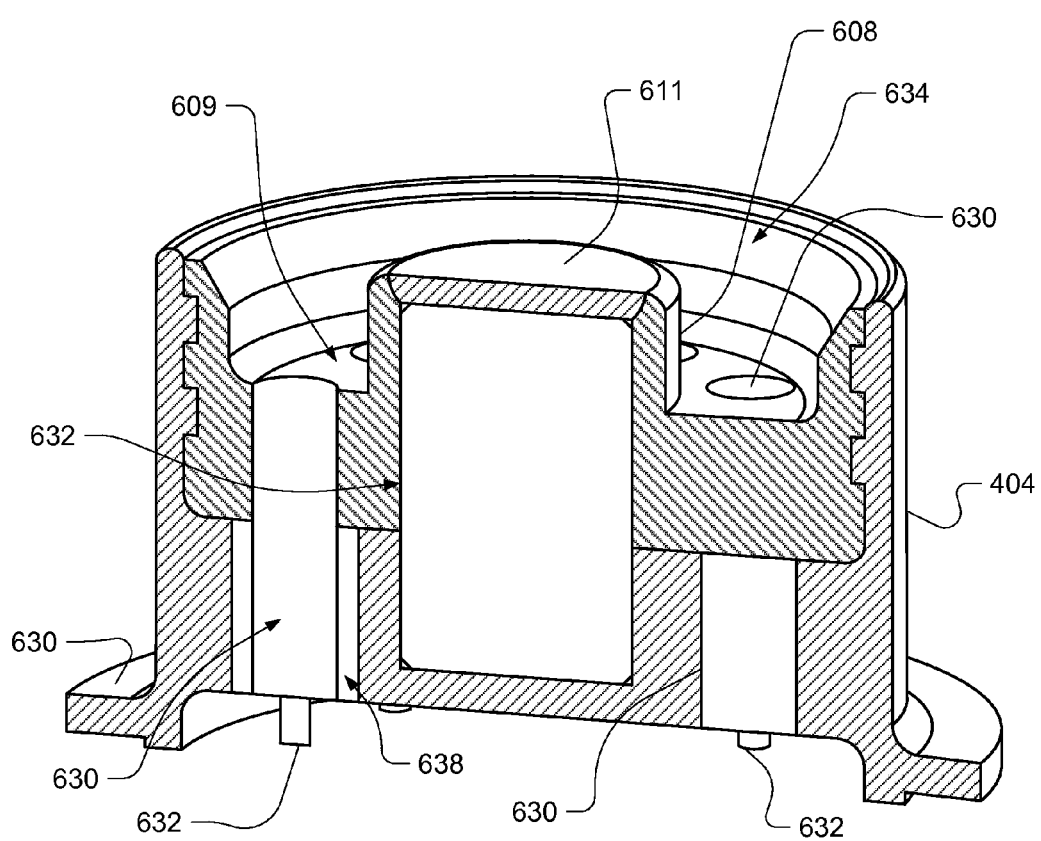
FIG. 19 shows a sectional view of the percutaneous port of FIGS. 16-18.

FIG. 19 shows a sectional view of the percutaneous port 404 of FIGS. 16-18. Embedded within the center of the protrusion 608, in accordance with this specific embodiment, is a rare earth magnet 632. The magnet 632 advantageously provides a sufficient force for holding a charging connector in place within the port's cavity 609. Provisions are provided for removing the magnet 632 in the event the user/patient needs to undergo an MRI examination. For example, a thin cover 611 may be placed over the magnet, which cover is removable, allowing the magnet 632 to be removed. The keyed slot 629 may be formed within the walls of the protrusion which holds the magnet 632. The thin cover 611 may also be formed to include the keyed slot 629.

FIG. 19 further shows that the contacts 630, of which there are eight in this embodiment, comprise relatively long cylinders that extend from a floor of the doughnut-shaped cavity 609 formed within the percuport 404 all the way through to the bottom connection pins 632, which are soldered, or otherwise attached, to the flexible PCB 620. Each of these eight contacts 630 are sealed with a ceramic or glass feed-through seal 638.

For the embodiment shown in FIG. 19, At least the interior surface of cavity 609 is made from a suitable non-conductive bio-compatible material, such as nylon or silicone. A mating connector (not shown in FIG. 19) includes spring mechanisms for making a good electrical contact with each of the contacts 630, as well as a mating magnet to hold the mating connector in place over the protrusion 608.

Figure 20:
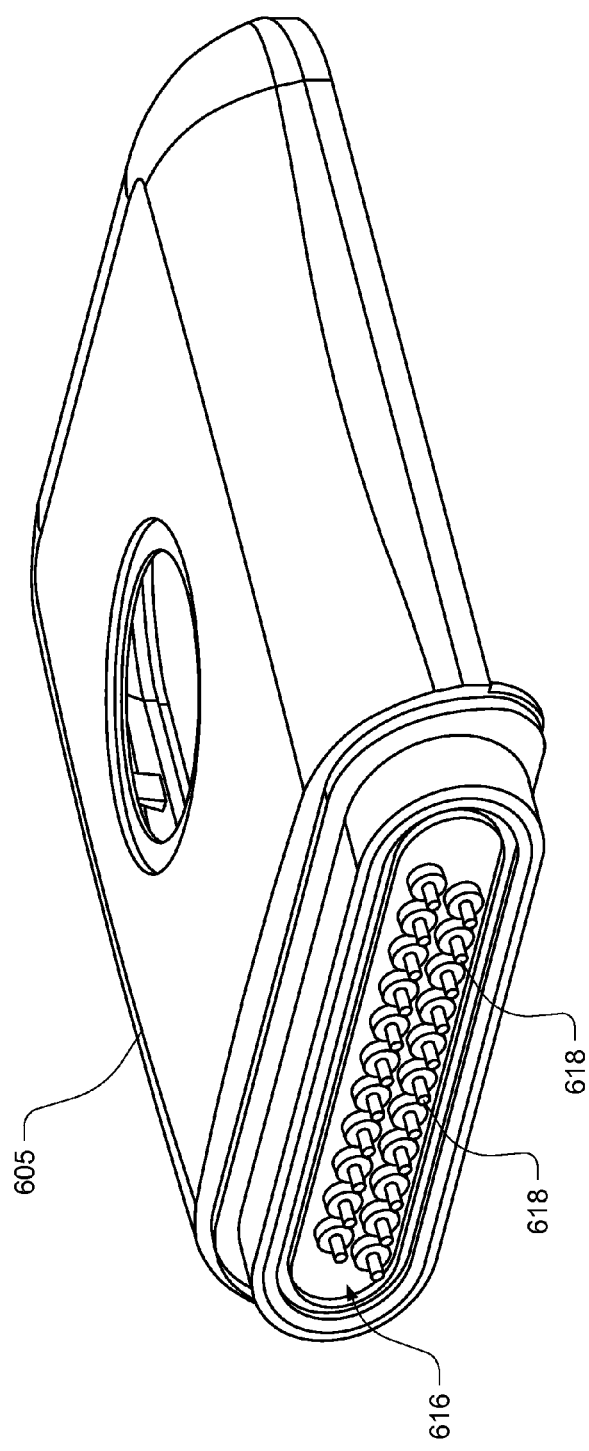
FIG. 20 is an ISO view of the cover and feedthru array, with the feedthru array welded in place to the cover, used with the PCIS of FIGS. 9-11.

FIG. 20 is an ISO view of the cover 605 and feedthru array 616, with the feedthru array 616 being welded in place to the cover 605.

Figure 21A:
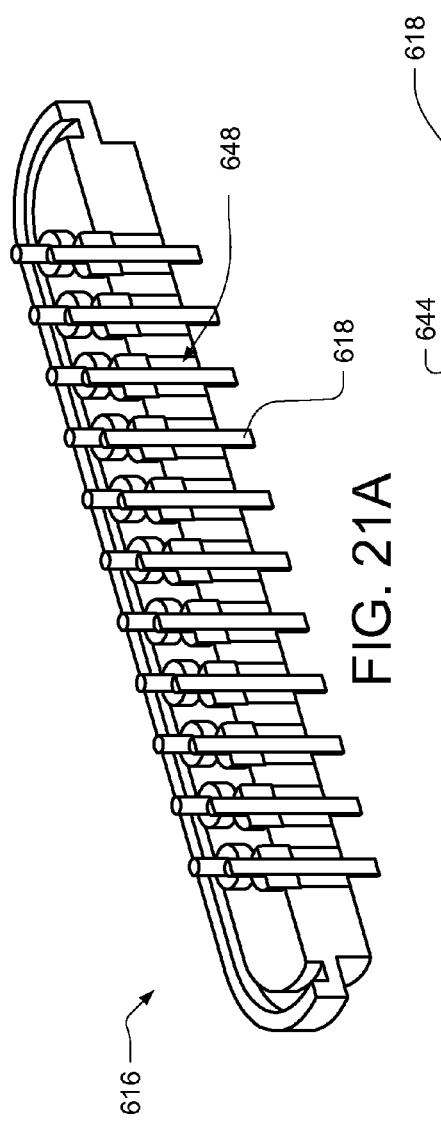
FIG. 21 shows an ISO sectional view (FIG. 21A), top view (FIG. 21B) and side view (FIG. 21C) of the feedthru array used with the PCIS of FIGS. 9-11.
Figure 21B:
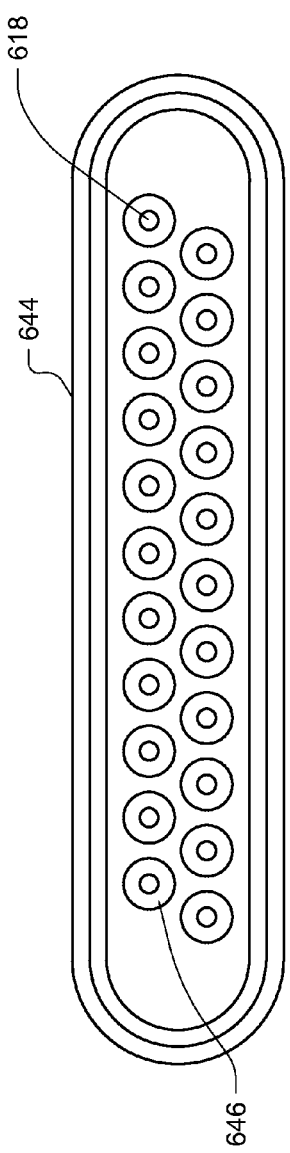
Figure 21C:
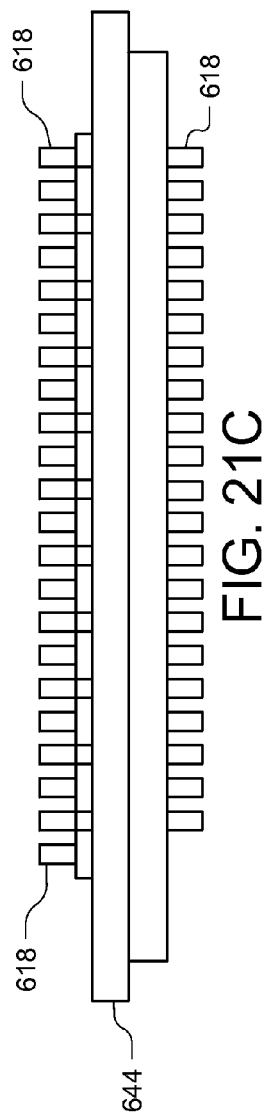
Figure 22:
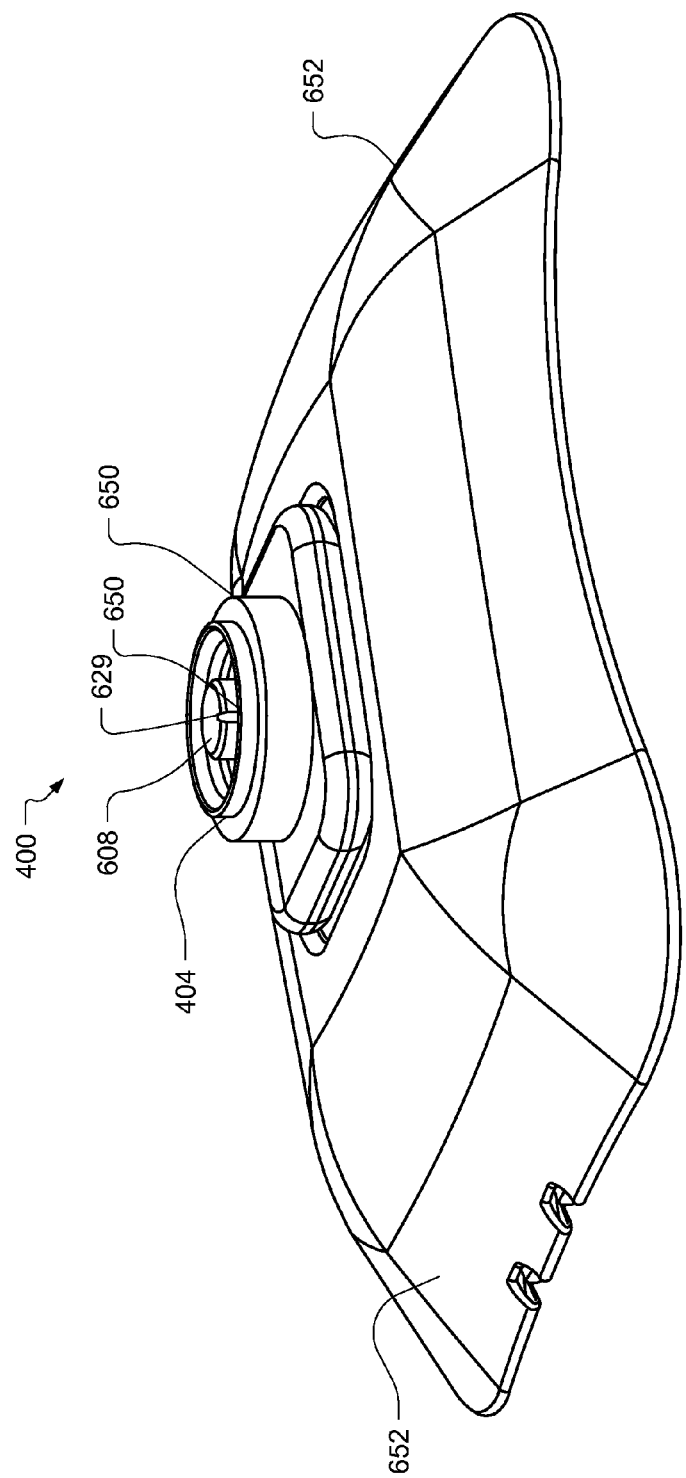
FIG. 22 shows an ISO view of the PCIS of FIGS. 9-11 after a silicone overmold has been applied thereto, and after a titanium mesh ring has been placed around the percuport.
Figure 23:
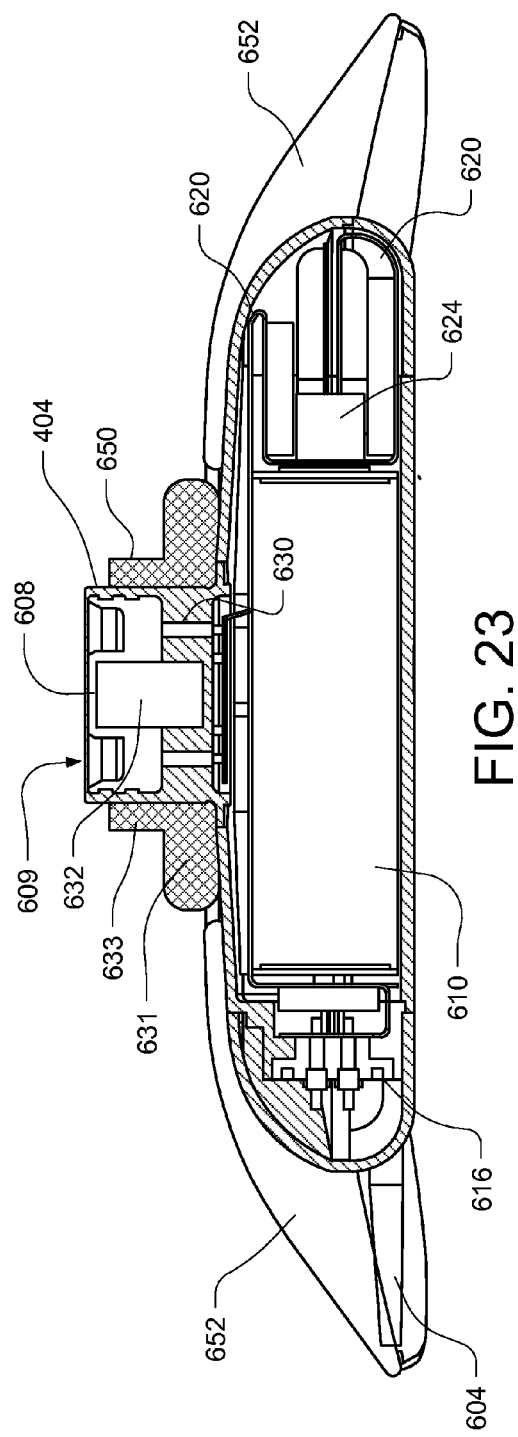
FIG. 23 is a side sectional view taken lengthwise through the center of the overmolded PCIS of FIG. 22.
Figure 24:
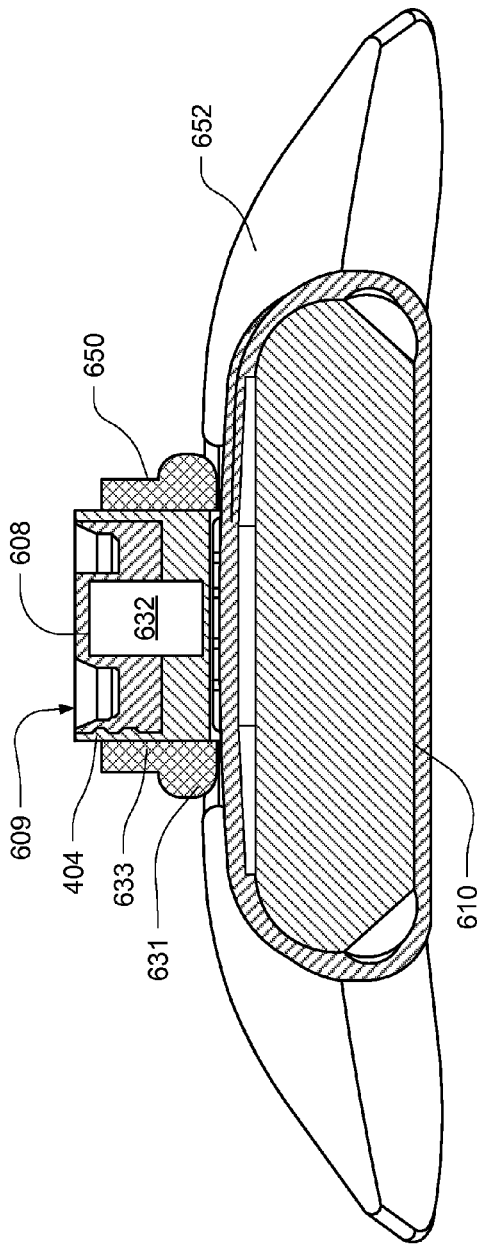
FIG. 24 is a side sectional view taken across the center of the overmolded PCIS of FIG. 22.
Figure 25:
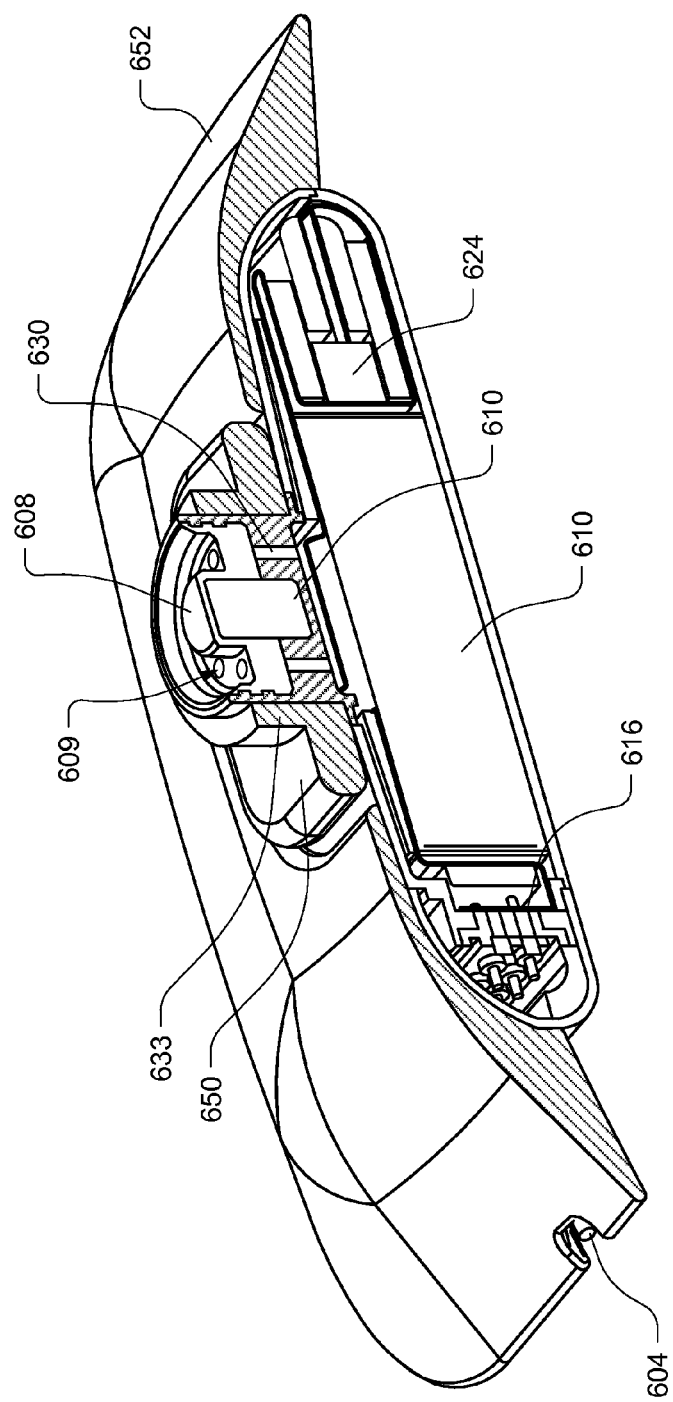
FIG. 25 is an ISO sectional view taken lengthwise through the center of the overmolded PCIS of FIG. 22.

FIG. 21 shows an ISO sectional view (FIG. 21A), top view (FIG. 21B) and side view (FIG. 21C) of the feed-through array 616 used with the PCIS 400 of FIGS. 9-11. A titanium frame 644 holds the twenty-two feed through pins 618 in a desired array pattern. A glass bead 646, reinforced with kryoflex to ensure a hermetic seal, insulates each pin 618 from the titanium frame 644. Other hermetic feed-throughs, such as ceramic feed-throughs, can be used. The titanium frame is then welded to the titanium case 605.

FIGS. 22, 23, 24 and 25 show respectively an ISO view, a lengthwise sectional view, a widthwise sectional view and an ISO sectional view of the PCIS 400 of FIGS. 9-11 after a silicone overmold 652 has been applied thereto, and after a titanium mesh ring 650 has been placed around the percuport 404. The mesh ring 650, as seen best in the sectional views of FIGS. 23-25, has a collar portion 631 near the base of the percuport 404, and a neck portion 633. Such features provide a larger surface area into which tissue ingrowth may occur, thereby promoting a good tissue seal and tissue vascularization around the percuport 404.

V. Exemplary Manual Control Methodologies

A Percutaneous Cochlear Implant System (PCIS) in accordance with the present inventions may be programmed and/or controlled in any suitable manner. For example, as described briefly previously in connection with FIG. 4, some implementations of the present PCIS may include module 428 adapted for insertion into the percuport 404, wherein module 428 may include an antenna (e.g., in combination with an FM receiver and/or BlueTooth® receiver) and receive instructions and/or programming information by way of a telemetric programmer. Some implementations of the present PCIS may include a data connector (e.g. a micro-USB connector within the module 434 that allows instructions and/or programming information to be received by way of a wired connection to a programmer.

Alternatively, or in addition, the percutaneous port 404 and a passive selector plug 422 may be configured to function as a user interface that allows attending medical personnel and/or the patient (user of the PCIS) to control various aspects of the operation of the PCIS and/or to input programming commands while implanted. This is accomplished by rotating the plug 422 relative to the percuport 404 in a prescribed direction for a prescribed amount in a prescribed sequence. For such rotation to generate the needed control signals, the percuport 404 has a pattern of contacts, e.g., contacts 170a and 170b, and contacts 172a and 172b, placed in the bottom of the cavity thereof. These contacts may be the same or similar as the contacts described previously in connection with FIGS. 15-19, but arranged in a pattern as illustrated, e.g., in FIGS. 30-35.

More specifically, in the exemplary implementation, the pair of contacts 170a and 170b comprise a control sensor 124, and the pair of contacts 172a and 172b comprise a control sensor 126. Together, these two pairs of contacts provide a pair of circumferentially spaced control sensors 124 and 126 embedded in the bottom or floor of the percuport 404. The passive selector plug 422, which functions when inserted into the percuport 404 as a rotatable cartridge, has a pattern of spaced metal (or conductive) surfaces, or sensible members 250, spaced around its bottom surface as shown in FIGS. 30-35. When the selector plug, or cartridge, 422 is inserted into the percuport 404, the conductive surface of the sensible members 250 makes electrical contact with none or both of the paired contacts of a given sensor 124 or 126. That is, the exemplary spaced sensible members 250 are electrically conductive pads. These electrically conductive pads either short together the paired contacts, or not, depending upon the rotational position of the cartridge on which the spaced sensible members 250 are placed. Thus, by monitoring the individual contacts associated with the contacts 170a and 170b (for sensor 124), and the contacts 172a and 172b (for sensor 126) with appropriate monitoring circuitry, it is possible to detect when the paired contacts 170a and 170b, or 172a and 172b, are shorted together (which occurs when the sensible member 250 is in contact with both contacts), or are not shorted together (which occurs when the sensible member 250 is not in contact with both contacts).

That is, a detectable short occurs between contact 170a and contact 170b when these contacts are both aligned with one of the electrically conductive pads 250. Similarly, a detectable short occurs between contact 172a and contact 172b when these contacts are both aligned with one of the electrically conductive pads 250.

Such sensing may advantageously be used by the circuitry within the PCIS to determine the direction and magnitude of the rotational movement of the cartridge (passive selector plug) 422 relative to the percutaneous port 404, as is discussed below with reference to FIGS. 30-35. The number of times there is (and is not) a short across contacts 170a/170b and contacts 172a/172b, and the order in which the short or open changes occur, is indicative of the magnitude and direction of the rotational movement of the cartridge 422 relative to the percutaneous port 404. The patient or other medical personnel may simply rotate the passive selector plug (cartridge) 422 in a predetermined manner to input commands and/or otherwise interface with the PCIS 400, as is discussed below with reference to FIG. 36.

In FIGS. 30-35, the exemplary sensible members 250 (which are spaced around a bottom or distal surface of the passive selector plug (or cartridge 422) are superimposed over an end wall 108 and control sensors 124 and 126 of the percutaneous port 404 in order to illustrate the changes in the relative rotational orientations of the sensible members and control sensors that occur when a cartridge 422 is located within the percutaneous port 404 of a PCIS and rotated relative thereto.

Figure 36:
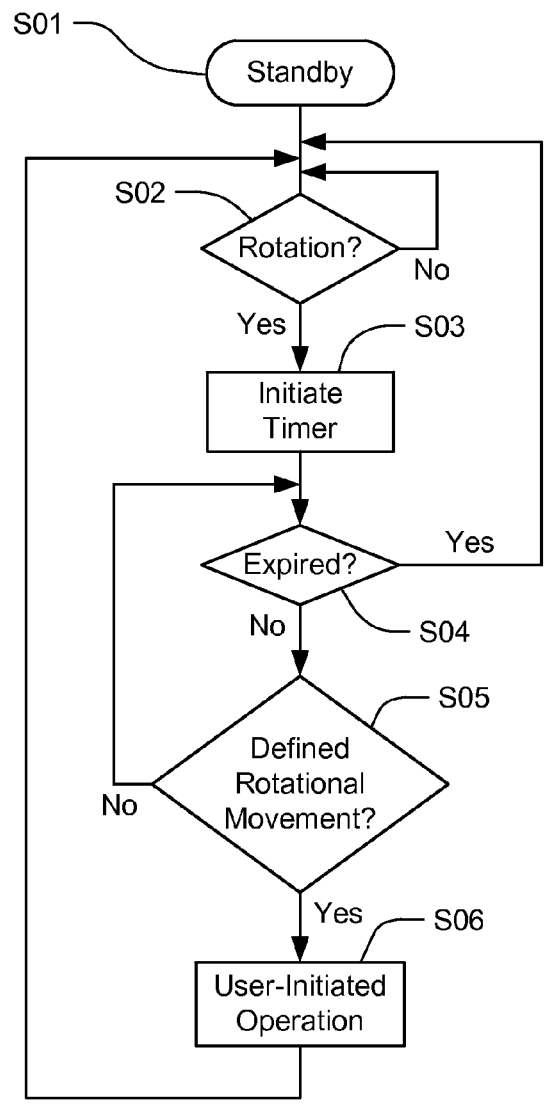
FIG. 36 is a flow chart that illustrates, in accordance with one embodiment of a present invention, how rotational direction and magnitude may be detected using a rotatable cartridge (or selector plug) inserted into the percutaneous port.

FIG. 36 illustrates the manner in which the direction and magnitude of the rotational movement of the passive selector plug 422 relative to the percuport 404 may be determined. FIG. 30 represents one exemplary initial orientation of the sensible members 250 and cartridge 422 (not shown) relative to the percutaneous port 404. No sensible member 250 is aligned with the contacts on either of the control sensors 124 and 126 in the illustrated rotational orientation and, accordingly, no sensible member is sensed at either of the control sensors (a "124-no/126-no" state). Of course, and as will be clear from the discussion below, the initial rotational orientation of the sensible members 250 (and cartridge 422) need not be that shown in FIG. 30.

In FIG. 31, the sensible members 250 (and cartridge 422) have been rotated relative to the percutaneous port 404 in the direction of arrow A such that the sensible member 250a is aligned with the contacts 172a/172b of control sensor 126 and no sensible member is aligned with the contacts 170a/170b of control sensor 124. A sensible member will, accordingly, not be sensed at control sensor 124 and will be sensed at control sensor 126 (a "124-no/126-yes" state). The transition from the 124-no/126-no state to the 124-no/126-yes state indicates that the sensible members 250 (and cartridge 422) are moving in the counter-clockwise direction.

Turning to FIG. 32, the sensible members 250 (and cartridge 422) have been further rotated relative to the percutaneous port 404 in the direction of arrow A such that the sensible member 250a remains aligned with the contacts 172a/172b of control sensor 126 and the sensible member 250a is now also aligned without the contacts 170a/170b of control sensor 124. A sensible member will, accordingly, be sensed at both control sensor 124 and control sensor 126 (a "124-yes/126-yes" state). The transition from the 124-no/126-yes state to the 124-yes/126-yes state, without reversion to the prior 124-no/126-no state, indicates that the cartridge 422 is continuing to move in the counter-clockwise direction without any appreciable movement in the clockwise direction.

In FIG. 33, the sensible members 250 (and cartridge 422) have been further rotated relative to the percutaneous port 404 in the direction of arrow A such that the sensible member 250a is no longer aligned with the contacts 172a/172b of control sensor 126 and the sensible member 250a remains aligned with the contacts 170a/170b of control sensor 124. A sensible member 250 will, accordingly, be sensed at control sensor 124 and not sensed at control sensor 126 (a "124-yes/126-no" state). The transition from the 124-yes/126-yes state to the 124-yes/126-no state, without reversion to the prior 124-no/126-yes state, indicates that the cartridge is continuing to move in a counter-clockwise direction without any appreciable movement in the clockwise direction.

A subsequent transition from the 124-yes/126-no state to the 124-no/126-no state (i.e. the initial state), without reversion to the prior state, will indicate that the movement has continued in the direction of arrow A and, in the context of the illustrated implementation, that there has been a single sensor cycle and that the cartridge has rotated a total of about 60 degrees from the initial location (FIG. 30). Continued rotation in the direction of arrow A to the location illustrated in FIG. 34, i.e. 180 degrees from the initial location (FIG. 30), will result in two more sensor cycles. Again, each sensor cycle is a transition from 124-no/126-no state to another 124-no/126-no state in the manner described above, and each cycle represents a rotation of 60 degrees (for the particular spaced orientation of the sensible members 250 shown in FIGS. 30-35).

It should be noted here that the 124-no/126-no state need not be the initial state when monitoring rotational movement of the passive selector plug 422 (or "cartridge" 422, as it is termed here for purposes of this discussion) relative to the percutaneous port 404. The initial state is merely the state present when rotational movement begins after a predetermined period without rotational movement (e.g. at least 5-10 seconds). If, for example, a sensible member 250 is aligned with the contacts on both of the control sensors 124 and 126, then the initial state will be the 124-yes/126-yes state, and a cycle will be a transition from a 124-yes/126-yes state to another 124-yes/126-yes state.

Rotational movement in the opposite direction is sensed in essentially the same way, although the yes/no transitions will occur in a different order. For example, FIGS. 34 and 35 show the rotation of the sensible members 250 (and cartridge 422) relative to the percutaneous port 404 in the direction of arrow B. The sensible member 250b will be sensed at control sensor 124 and not sensed at control sensor 126 in FIG. 35. The transition from the 124-no/126-no state (FIG. 34) to the 124-yes/126-no state (FIG. 35) indicates that the cartridge is moving in a clockwise direction.

Regardless of the type of sensors and sensible members that are employed, and the manner in which the sensors and sensible members are used to identify rotational movement of the selector plug (or cartridge) 422 relative to the percutaneous port 404, the ability to identify and track such rotational movement facilitates the use of the percutaneous port and the cartridge as a user interface. By way of example, but not limitation, a variety of user-initiated implantable medical device operations may be pre-programmed into the partially implantable medical device and such operations may be actuated by the port/cartridge user interface. Each user-initiated operation may be assigned a unique defined cartridge rotational movement or a unique defined combination of rotational movements (collectively "defined cartridge rotational movement"). A time limit may be applied in at least some embodiments. For example, a defined cartridge rotational movement may be deemed ineffective unless the combination is completed within a predetermined time period (e.g. about 15 seconds from the initial detection of rotation).

The general operation of the user interface and the associated aspects of the control circuitry used to detect the relative magnitude and direction of the rotation of the selector plug 422 (or cartridge 422) is graphically illustrated in the flow chart of FIG. 36. More specifically, with respect to user-initiated operation, the control circuitry 360 will remain in a standby state (step S01) until rotational movement of the cartridge is sensed (step S02). A timer is initiated in response to the sensing of cartridge rotation (step S03). If one of the defined cartridge rotational movements is received prior to the expiration of the predetermined period (steps S04 and S05), then the user-initiated operation associated with the defined cartridge rotational movement will be initiated (step S06). If, on the other hand, one of the defined cartridge rotational movements is not received prior to the expiration of the predetermined period (steps S04 and S05), the control circuitry will return to the standby state with respect to the user interface aspects of its operation.

For example, an operation may be initiated in response to the following cartridge rotational movement: at least 360 degrees in one direction followed by rotation of at least 360 degrees in the opposite direction, with both rotations occurring within 15 seconds of the initiation of the first rotation. Another exemplary rotation combination is rotation of at least 180 degrees in a particular direction that is completed within 15 seconds of the initiation of the rotation. The control circuitry may also be configured to actuate an audible and/or vibratory alarm (not shown) that is located within the housing 408 (FIG. 4) in response to a successful input of a defined cartridge rotational movement and/or an unsuccessful input attempt. Different versions of the alarm (e.g. one beep vs. two beeps) may be used when the alarm is actuated in response to both successful and unsuccessful attempts.

With respect to the user-initiated operations themselves, one example involves turning the PCIS on or off. Turning the PCIS on/off is somewhat of a misnomer because at least some circuits of the PCIS are always on. What typically occurs when a user decides to turn his or her PCIS "off" is that most of the microphone and amplifier circuits in the sound processor portion are put in a sleep state, or the stimulation circuits are shut down, so that the user does not receive any stimulation until such circuits are turned "on", or placed in an "awake" state.

Another exemplary user-initiated operation is volume adjustment. To activate volume adjustment, for example, a user may rotate the cartridge 422 a prescribed amount, e.g., 60 degrees, in one direction followed within a few seconds by rotation in the other direction by the same amount. Then, once volume control has been activated, a clockwise rotation of the cartridge would be interpreted by appropriate control circuitry as a desire to increase the volume of sound that is perceived (i.e., a command to increase the stimulus level), whereas a counter-clockwise rotation of the cartridge would be interpreted as a desire to decrease the volume of sound that is perceived (i.e., a command to decrease the stimulus level).

There are a variety of advantages associated with a user interface that is defined by the percutaneous port 404 and cartridge or plug 422 inserted therein. By way of example, and not by limitation, the present user interface obviates the need for the patient or user to possess a telemetric remote control and, accordingly, obviates the expense and potential inconvenience (if lost or otherwise unavailable) associated with a remote control. The present user interface may also eliminate the need for telemetric control for programming by the physician, or other medical personnel, thereby eliminating the need for an antenna and associated telemetric circuitry in the partially implantable medical device.

VII. Additional Exemplary Implementations

As described previously in connection with FIGS. 3-6, a wide variety of configurations of a Percutaneous Cochlear Implant System (PCIS) may be realized using a percutaneous port 404 as the interface between the external components of the system and the implanted components of the system. Moreover, because some of the components of the system, e.g., some circuitry, a battery, or a selector plug (that provides a user interface for operation and control of the PCIS) may actually be removably housed within the percuport 404, such components offer many of the advantages of functioning as quasi-implantable components (i.e., once inserted into the percuport 404 the user does not have to worry about them, or deal with connectivity issues; rather, these components are just always there as part of the system, like the implantable components are). At the same time, such components placed inside of the percuport offer the same advantages as external components, i.e., they can be easily upgraded, replaced and/or adjusted or tuned as needed, without the expense and risk of surgery.

In some configurations, as shown in FIG. 4, a power source module 424 may be selectively removable from port 404. This allows the user to easily remove and replace a power source, e.g., a battery, when the energy contained therein has been depleted.

Additionally, or alternatively, a battery, or other power source, contained within power source module 424 may be rechargeable. For example, a charger may be coupled to a proximal end of a power source module 424 and/or to a connector disposed within port 404, which connection allows power within the power source module 424 to be replenished. Such recharging may be accomplished, e.g., through "earphones" having a charging circuit formed therein, with a separate cable configured to be electrically coupled to power source module 424 and/or by any other charging circuit (e.g., inductive coupling through a charging coil) as may serve a particular application. In some examples where headphones are used to recharge power source 424, such headphones may also be configured to allow the patient to listen to music or other audio sounds during the charging session.

When a power source module 424 is the only component housed within percuport 404, the size of the power source, e.g., battery, contained therein may be increased so as to provide relatively more power to implanted circuits 408. (FIG. 4). Alternatively, a relatively small power source module 424 may be used so that the size of port 404 may be minimized where easily replaceable and inexpensive power source modules 424 exist.

Figure 26:
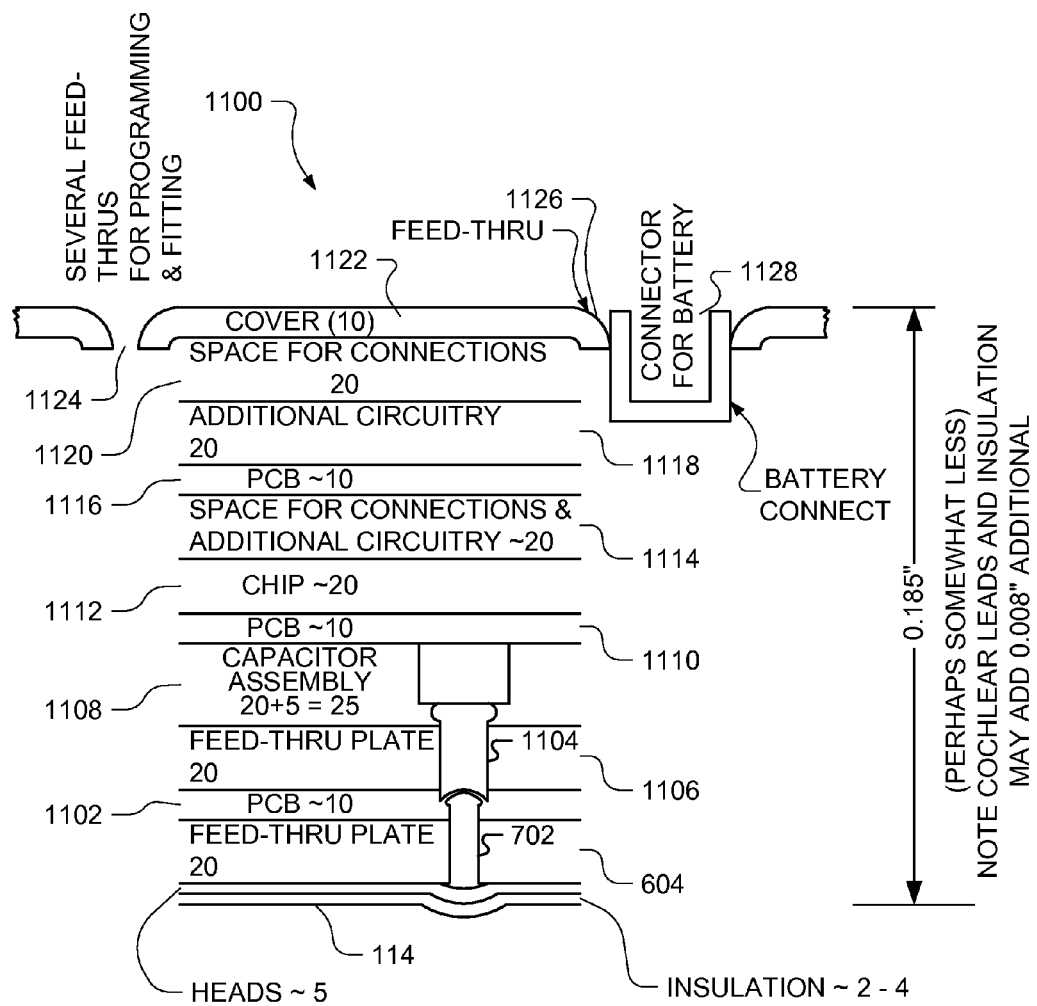
FIG. 26 is a cross-sectional side view of an exemplary stack-up configuration within a percutaneous port wherein a stimulation module that includes both a speech processor and a cochlear stimulator is housed.

Turning to FIG. 26, a cross-sectional side view of an exemplary stack-up configuration 1100 is illustrated that may be used within port 404 for a configuration wherein a stimulation module 1006 includes both speech processor 106 and cochlear stimulator 110. The stack-up configuration 1100 shown in FIG. 26 is merely illustrative of one of the many different stack-ups that may be used to serve a particular application.

As shown in FIG. 26, stack-up configuration 1100 may include various layers of components. For example, a first layer may comprise feedthrough plate 604. Feedthrough plate 604 may include one or more electrical vias 702 (shown in FIG. 26 as feedthrough pins). A distal side of electrical via 702 may be coupled to an electrode lead 114, which may be implanted within the patient (e.g., within a surgically created tunnel that directs the lead to the cochlea of the patient's inner ear).

Above feedthrough plate 604, a relatively small space 1102 exists formed by electrical via 702 and a corresponding conductive pin 1104 that is a part of another feedthrough plate 1106. Feedthrough plate 1106 may have various electrical components mounted thereon. Various other layers 1108 through 1120 are shown in FIG. 26 for illustrative purposes. Each layer may have additional components or interconnections carried thereon, much like a multi-layer circuit board. A cover 1122 is configured to hermetically protect layers 604 through 1120, as well as the components carried thereon, e.g., a capacitor assembly 1108, printed circuit board layer 1110, and chip layer 1112. Various feedthroughs 1124 and 1126 and a power supply connector 1128 may also be included in the stack-up configuration 1100.

Figure 27:
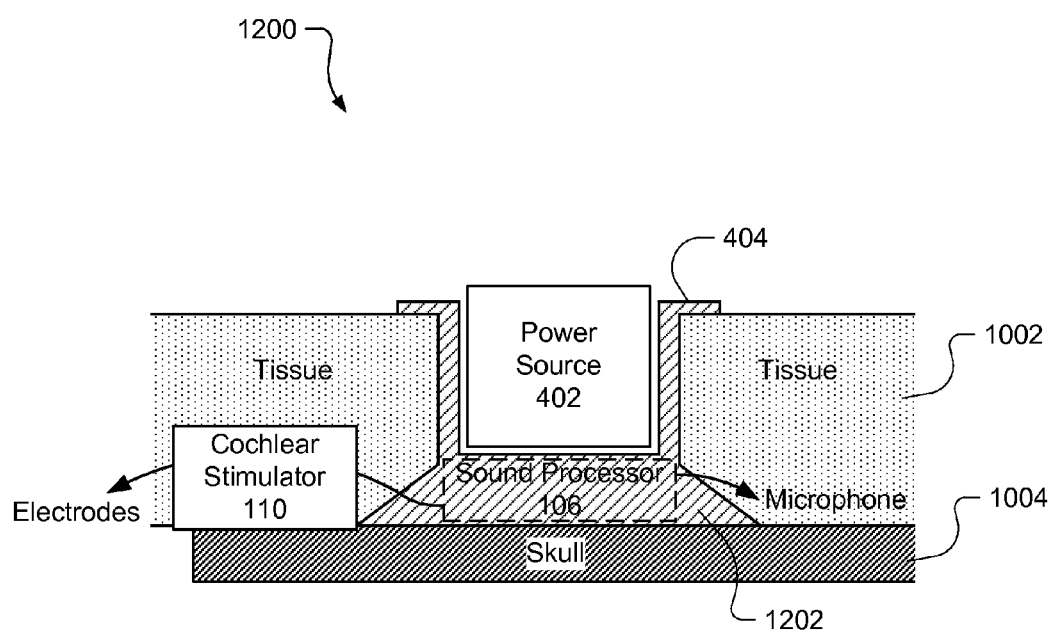
FIG. 27 is a schematic diagram that illustrates an exemplary embodiment of the PCIS wherein the percutaneous port includes an enlarged distal cavity configured to house the sound processor.

Next, as schematically illustrated in FIG. 27, a particular configuration of a percutaneous cochlear implant system (PCIS) is shown wherein percutaneous port 404 includes an enlarged distal cavity 1202 configured to house a sound processor 106. An implantable cochlear stimulator unit 110 connects to the sound processor 106, as does an implantable microphone 108.

A relatively larger distal cavity 1202 of percutaneous port 404, as schematically shown in FIG. 27, may be desirable in some instances, e.g., in order to fit certain types of sound processors 106 therein. For example, the circuitry associated with existing and approved sound processors 106 may be housed within the enlarged distal cavity 1202. Being able to use existing and approved sound processing circuitry can prove to be a significant advantage relative to the time it takes to get a PCIS to market.

As seen in FIG. 27, the PCIS shown therein includes a percutaneous port 404 having a sound processor 106 housed in an enlarged distal cavity 1202 thereof. A power source 402 is inserted into the port 404 so as to reside above the cavity 1202 and can be removed from port 404, as needed, to be replaced and/or recharged. Recharging of power source 402 could also occur without removing power source from the port 404. Enlarged distal cavity 1202 is preferably circular in cross-section with a diameter relatively larger than that of a proximal portion of port 404. It should be noted, however, that distal cavity 1202 may have cross-sectional shapes other than circular in order to, for example, accommodate a sound processor 106 and/or other components that are oval, square, rectangular, or otherwise shaped.

Figure 28:
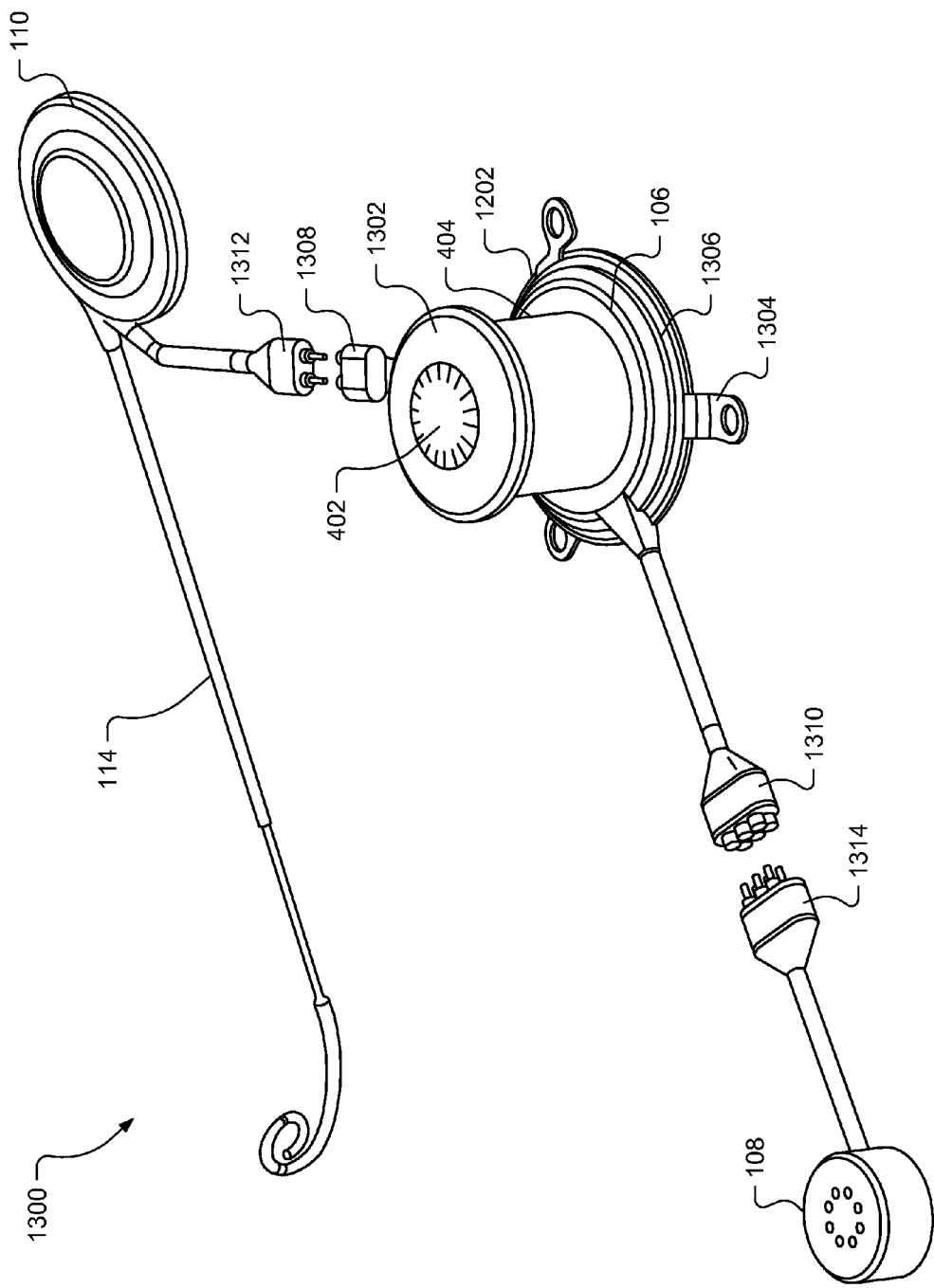
FIG. 28 is a perspective view of one exemplary configuration of the PCIS schematically depicted in FIG. 27. A titanium mesh sleeve, not shown in FIG. 28, surrounds the percuport 404.

FIG. 28 is a perspective view of an exemplary configuration 1300 of percutaneous cochlear implant system 400 such as the one shown in FIG. 27, i.e., one employing an enlarged cavity 1202 at the distal end of the percutaneous port 404. In configuration 1300, port 404 is configured to house power source 402 in a proximal portion thereof and sound processor 106 in an enlarged distal cavity 1202 thereof. A cap assembly 1302 is provided to protect the interior of port 404 from exposure to one or more elements. Cap assembly 1302 is described in more detail below. One or more attachment flanges 1304 may be optionally coupled to distal cavity 1202, as shown in FIG. 13, to facilitate affixation of port 404 to the skull of a patient.

In some examples, a silicone rubber molding 1306 partially surrounds distal cavity 1202. Such molding 1306 serves to provide additional protection for distal cavity 1202, as well as protection for the tissue in which the port 404 is implanted.

As shown in FIG. 28, one or more connector assemblies (e.g., connector assemblies 1308 and 1310) may be coupled to port 404. As will be described in more detail below, connector assemblies 1308 and 1310, when used, allow detachable electrical connection to be made between components housed within the sound processor cavity 1202 and components housed outside of the sound processor cavity 1202. For example, connector assembly 1308 is adapted to mate with connector assembly 1312 in order to electrically connect an implanted cochlear stimulator assembly 110 with the speech processor 106. As seen in FIG. 28, an electrode lead, with an electrode array located along its distal end, is also connected to the cochlear stimulator assembly 110. Similarly, connector assembly 1310 is adapted to mate with connector assembly 1314 in order to electrically connect a microphone assembly 108 with the speech processor 106.

The electrical connections made to components housed within the sound processor cavity 1202 occur through corresponding electrical vias (e.g., conductive feedthrough pins, or "feedthrus") that pass through the walls of cavity 1202. The type of feedthrough pins used for this purpose may be of conventional design. A preferred location for these pins is shown in FIG. 29A, discussed below.

As indicated previously, connector assembly 1308 is configured to facilitate detachable connection between cochlear stimulator 110 and sound processor 106, which is housed within port 404. To this end, connector assembly 1312 is configured to detachably connect with a mating connector assembly 1308. Because connector assembly 1312 is connected to cochlear stimulator 110 and connector assembly 1308 is connected to sound processor 106, the joining together of connector assembly 1308 with connector assembly 1312 allows the desired electrical/signal connection to be made between cochlear stimulator 110 and sound processor 106. At least two conductors will typically be required to make this connection between the sound processor 106 and the cochlear stimulator 110, with both power and data being sent over these two conductors, e.g., with power comprising a first signal, and with data comprising appropriate modulation applied to the first signal.

In a similar manner, connector assembly 1310 is configured to facilitate detachable connection between microphone 108 and sound processor 106, which is housed within port 404. To this end, connector assembly 1314 is configured to detachably connect with a mating connector assembly 1310. Because connector assembly 1314 is connected to microphone 108 and connector assembly 1310 is connected to sound processor 106, the joining together of connector assembly 1314 with connector assembly 1310 allows the desired electrical connection to be made between microphone 108 and sound processor 106. At least five conductors will typically be required to make this connection between the sound processor 106 and the microphone 108, although any number of conductive paths may be used to electrically couple microphone 108 to sound processor 106.

Figure 29A:
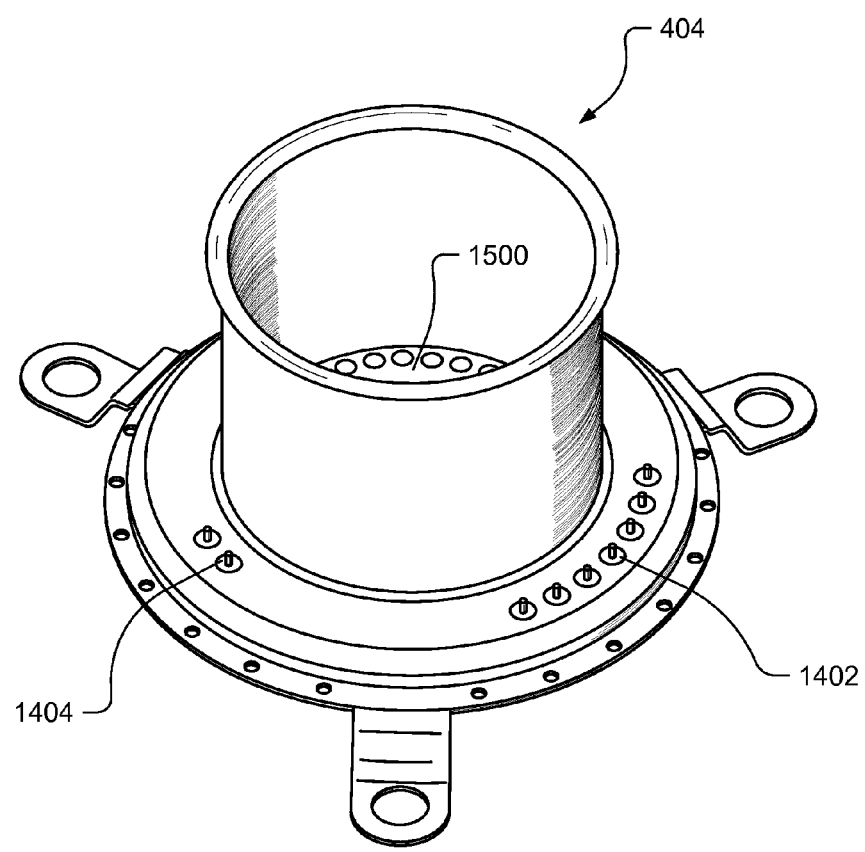
FIG. 29A is a top perspective view of percutaneous port 404, absent the titanium mesh sleeve that surrounds it, after a feedthrough plate 1500 has been coupled to a distal ridge thereof.

FIG. 29A is a top perspective view of port 404 after a feedthrough plate 1500 has been coupled to ridge of port 404. As seen in FIG. 29A, feedthrough pins 1402 extend around the perimeter of the enlarged distal cavity port 404. These feedthrough pins provide the means for electrical cable/connector 1310 and electrical cable/connector 1308 to make electrical contact with the circuits housed within the distal cavity 1202 of percutaneous port 404.

Figure 29B:
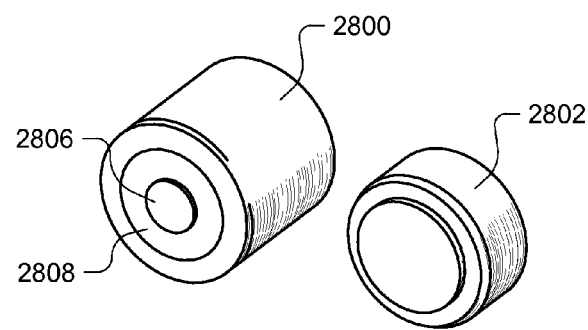
FIGS. 29B and 29C depict representative power sources 2800 and 2802 that may be inserted within a battery cartridge, which battery cartridge may then be inserted into the cavity of percutaneous port 404, and thereafter used to provide operating power for the percutaneous cochlear implant systems and methods described herein.
Figure 29C:
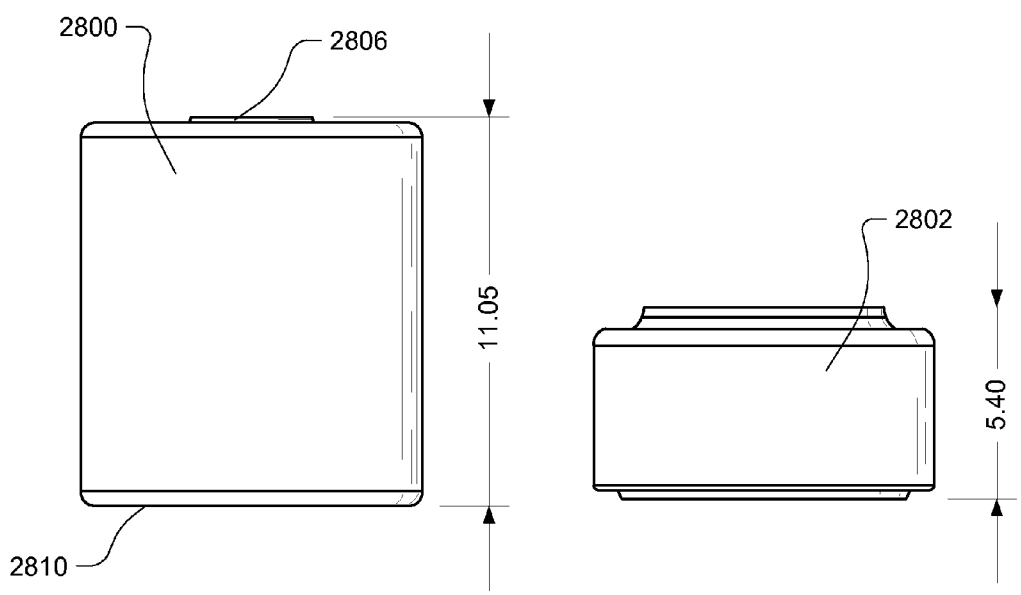

FIGS. 29B-29C illustrate various power sources 2800 and 2802 that may be inserted within port 404 and used in connection with the systems and methods described herein. Dimensions in millimeters shown in FIG. 29C are exemplary only. Power source 2800 may comprise a rechargeable lithium ion battery operating at 3.6 volts with a capacity of about 40 mAh. Power source 2802 may comprise a zinc-air battery operating at 1.4 volts with a capacity of 650 mAh. It will be recognized that power sources 2800 and 2802 are merely illustrative of the many different power sources that may be used in connection with the systems and methods described herein.

Figure 29D:
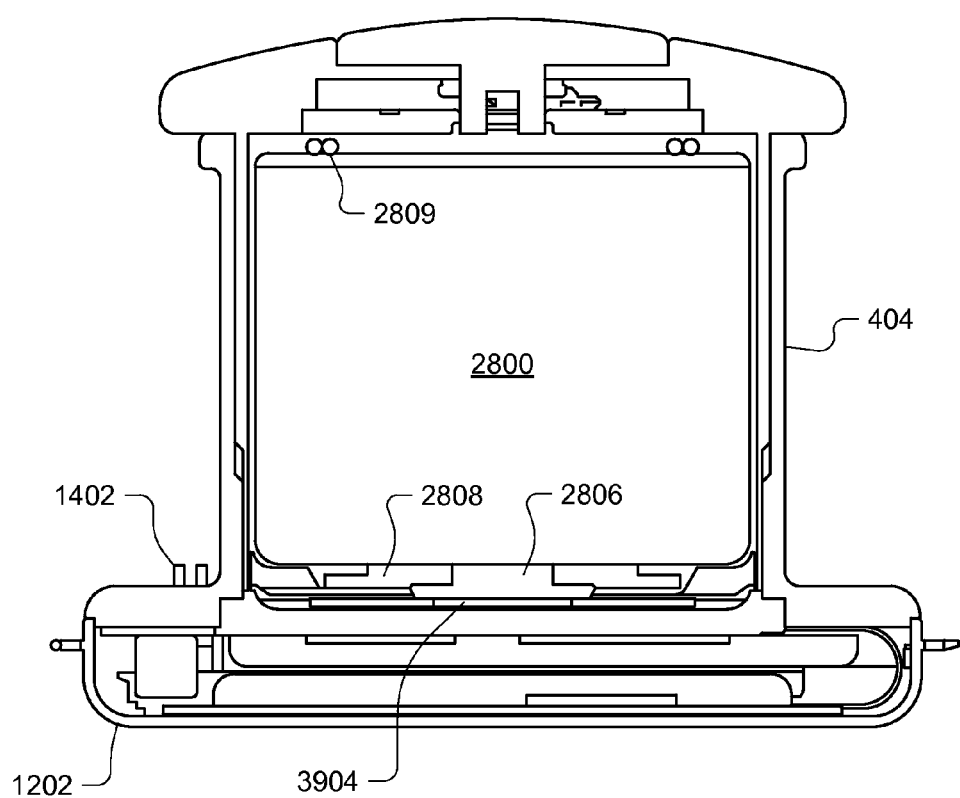
FIG. 29D is a cross-sectional side view of a fully loaded and assembled percutaneous port 404. This cross-sectional side view illustrates a larger lithium ion battery, having a voltage of 3-4 volts, filling the cavity within the percutaneous port.
Figure 29E:
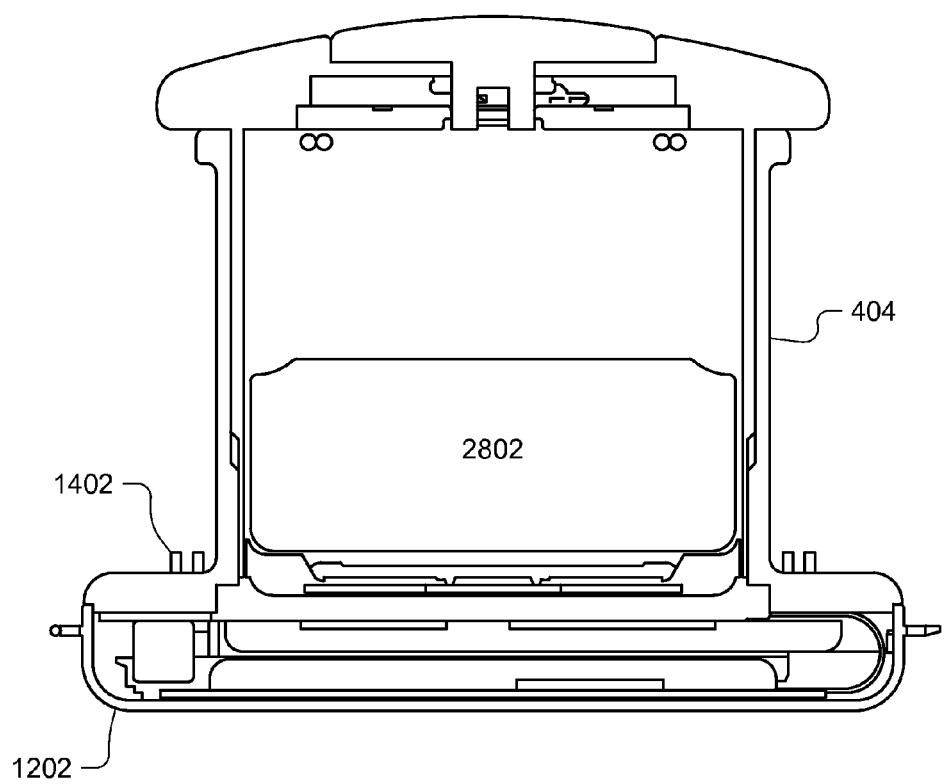
FIG. 29E is a cross-sectional side view of a loaded and assembled percutaneous port 404 as in FIG. 40, but wherein a different size battery, e.g., a zinc-air battery, is inserted into the battery cartridge assembly. Two or three stacked zinc-air batteries may be inserted into the battery cartridge assembly to increase the voltage.

FIGS. 29D and 29E depict sectional views of the percutaneous port 404 having batteries loaded therein. As seen in FIG. 29D, for example, a full size battery 2800 is inserted therein as its power source. A full size battery, for purposes here, is a battery that fills all (or substantially all) of the space within the battery portion of the percutaneous port 404. The battery 2800, as seen best in FIGS. 29B and 29C, has two terminals, a first terminal 2806, which is located in the center of a first end thereof (shown as the "top" end as oriented in FIG. 29C), and a second terminal 2810 which generally comprises the entire metal case of the battery, except for the first terminal portion. An insulative annular ring 2808 is formed within the wall of the battery housing to electrically insulate or separate the first terminal 2806 from the second terminal 2810 when the battery is inserted into the battery housing. As shown in FIG. 29D, a preferred placement of the battery into its housing is with the first end thereof against the distal end of the housing, i.e., with the first terminal 2806 being held against the "bottom" side of the battery housing as depicted in FIG. 29D. Any suitable means may be employed to securely hold the battery in this position, e.g., a flattened coil spring 2809 (flattened by closure of a removable top cover) after the battery 2800 has been inserted into the port 404.

As thus seen in the sectional view of FIG. 29D, when the battery 2800 is fully inserted into the battery portion of percutaneous port 404, the centrally located battery terminal 2806 makes contact with a terminal 3904 located at the distal end of the cavity formed by the percuport 404. Electrical contact with the second terminal 2810 of the battery 2800 can be made at any location on the battery case.

FIG. 29E is a sectional view of percutaneous port 404 similar to FIG. 29D, but includes the smaller power source 2802 In FIG. 29E, for example, power source 2802 may comprise a stack of zinc-air batteries 4102, only one of which is shown in FIG. 29E to give perspective of the relative size of the zinc-air battery.

Figure 37:
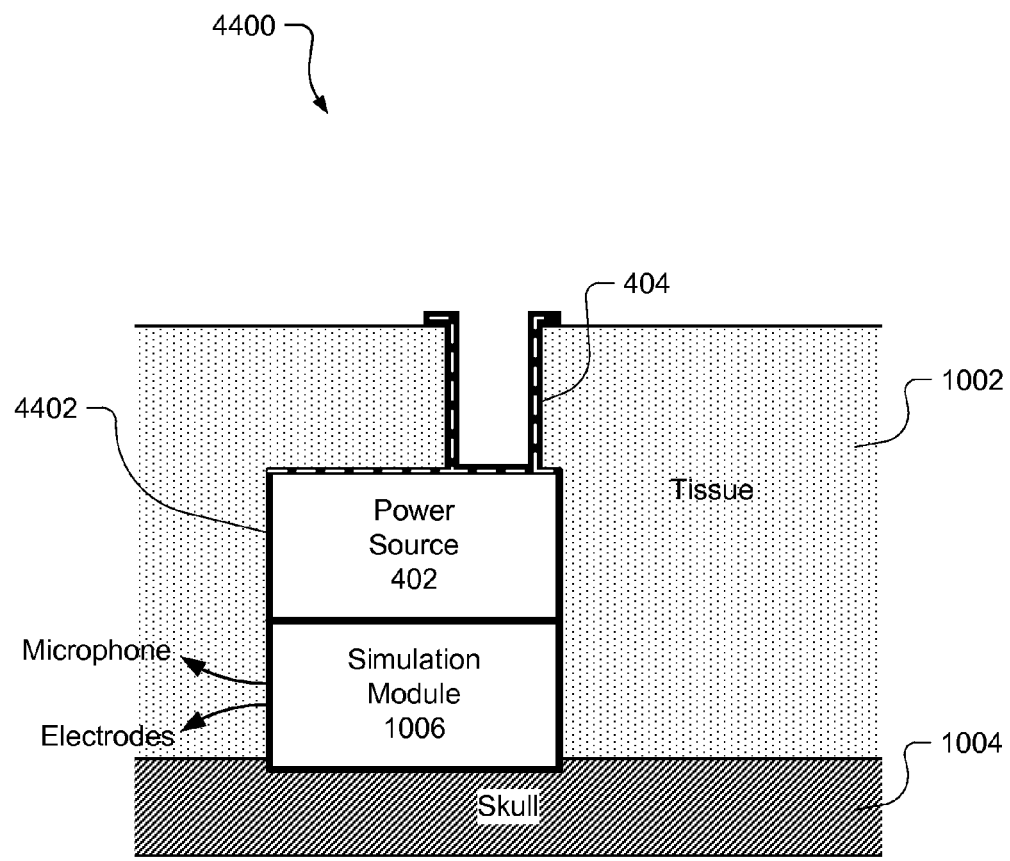
FIG. 37 illustrates another implant configuration or embodiment of the invention, similar to the embodiment shown in connection with FIGS. 9-25, wherein both a power source 402 and a stimulation module 1006 are entirely implanted within the patient outside of the percutaneous port 404.

Turning next to FIG. 37, there is illustrated, in schematic fashion, an exemplary implant configuration 4400 wherein power source 402 and stimulation module 1006 are entirely implanted within the patient outside of percutaneous port 404. This is similar to the schematic relationship provided by the preferred embodiment of a PCIS described previously in connection with FIGS. 9-25. As shown in FIG. 37, power source 402 and stimulation module 1006 are included within the same module 4402. Moreover, circuitry for performing the functions of the sound processor and the cochlear stimulator of a cochlear stimulator system are contained within the stimulation module 1006. Module 4402 may be of any suitable shape or size. A key advantage of the configuration shown in FIG. 44 is that existing and approved implantable power sources, as well as existing and approved sound processing and cochlear stimulator circuitry, may be used to realize a cochlear stimulator system as described.

As shown in FIG. 37, percutaneous port 404 may be coupled to a top surface of module 4402. In this manner, port 404 may be used to control, access, and/or otherwise communicate with one or more components within module 4402.

Figure 38A:
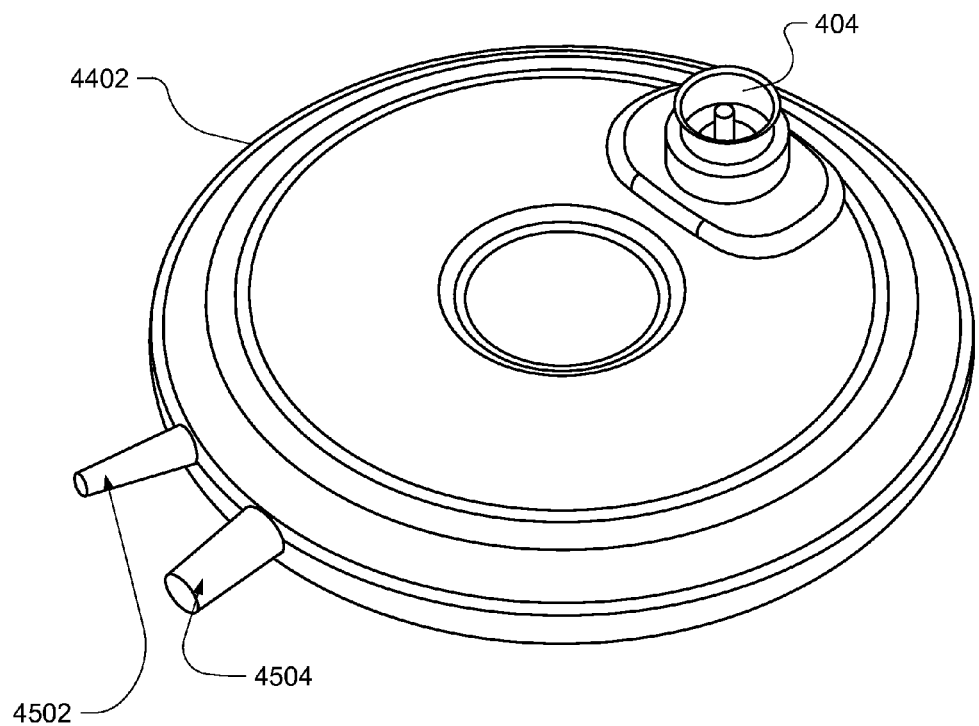
FIG. 38A shows one possible configuration of the percutaneous implant system of FIG. 37 wherein the percutaneous port 404 is coupled to a top surface of an implantable stimulation module 4402, and wherein a power source and all requisite electronic circuitry are housed within the stimulation module.

To illustrate, FIG. 38A is a perspective view of an exemplary module 4402 having a generally circular or disk shape. (It is to be noted that this shape could also be oval-shaped, or rectangular-shaped, or any other suitable shape, rather than circular or disk-shaped.) The percutaneous port 404 is coupled to a top surface of the disk-shaped housing 4402. Cables 4502 and 4504 (only partially shown in FIG. 45A) exit from a side or perimeter of the housing 4402. Cable 4504, for example, is where a cochlear implant lead and electrodes may be attached to the module; while cable 4502 is where a microphone may be attached to the module.

Figure 38B:
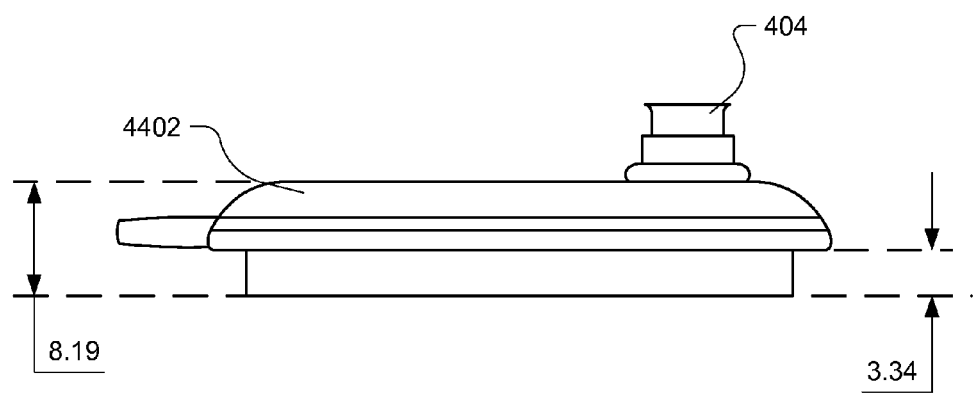
FIG. 38B is a side view of the stimulation module 4402 shown in FIG. 38A.

FIG. 38B is a side view of the module 4402 shown in FIG. 38A. Exemplary dimensions of the module 4402 are 8.19 mm (approx. 8.2 mm) thick by about 46.5 mm in diameter. The percutaneous port 404 extends about 6.33 mm above the surface of the module 4402. With advanced assembly the overall thickness of the module may be reduced to less than 6 mm.

Figure 39:
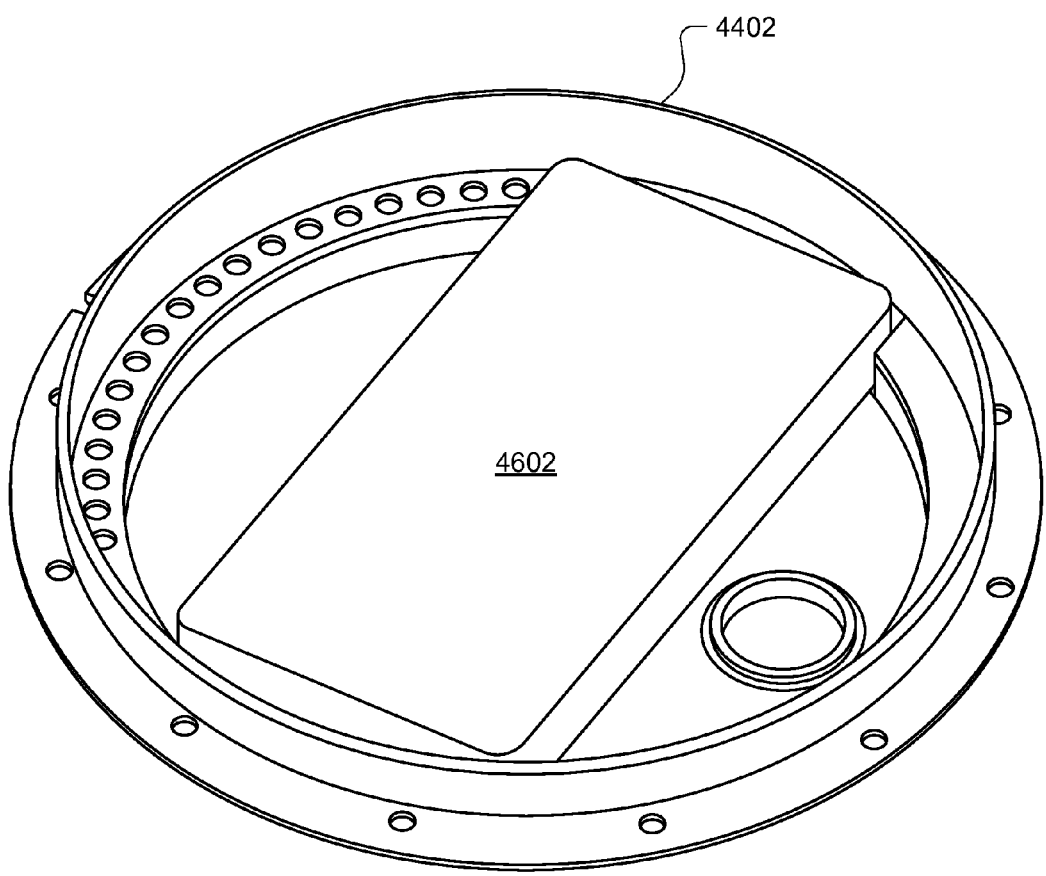
FIG. 39 shows the manner in which a commercially available rechargeable battery may be housed within the stimulation module 4402 of FIG. 38A.

FIG. 39 illustrates how an approved and existing implantable, rechargeable battery 4602 having a generally rectangular shape may be housed in a battery portion of the circular, or disc-shaped module 4402. One approved implantable battery 4602 that may be used with the PCIS described herein has a length L1 of about 35 mm, and a width W1 of about 17 mm. Moreover, it has a height H2 of about 5.5 mm. Such battery is manufactured by QUALLION, of Sylmar, Calif., as model number QL02001-A.

Figures 40A, 40B:
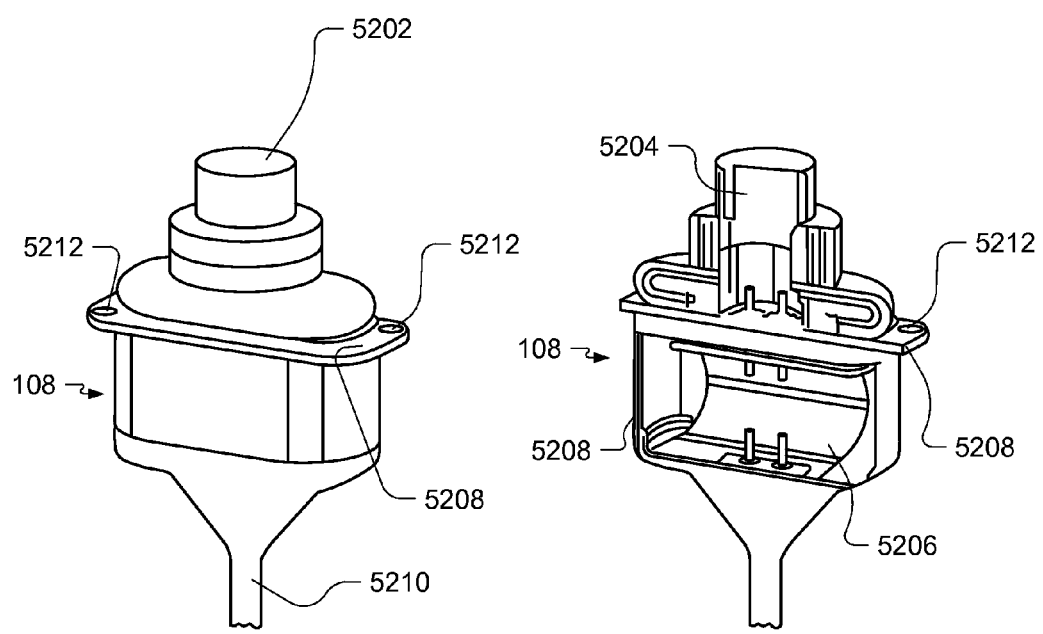
FIGS. 40A and 40B illustrate a perspective and sectional view, respectively, of an exemplary microphone that may be implanted within the ear canal of a patient, or elsewhere within or on the head of patient, and used to sense audio sound signals, transduce them to electrical signals, and provide the sensed electrical signals to the circuitry housed within the PCIS.

Turning next to FIG. 40A, there is shown an exemplary microphone assembly 108 that may be used with the percutaneous cochlear Implant system configurations described herein. FIG. 40B is a sectional view of the microphone assembly 108 shown in FIG. 40A. The microphone assembly 108 includes a microphone membrane 5202 coupled to an appropriate microphone transducer 5204. The transducer 5204 is adapted to convert mechanical vibrations associated with sound waves (or sound vibrations) striking or impacting the membrane 5202 into electrical signals. The electrical signals are then processed (e.g., amplified and filtered) as needed. The processed signals are then coupled to the sound processor of the cochlear implant system over a suitable cable 5210 that may connect directly with, e.g., cable/connector 1310 (of FIG. 28) or with the cable 4504 (of FIG. 38A).

A flex circuit 5206 may reside within a housing 5208 of the microphone assembly 108 to help hold and connect electronic components associated with operation of the microphone assembly 108. Such operation includes performing the signal processing function (e.g., amplification and filtering) carried out by the microphone assembly 108 as sound waves are sensed or detected through the membrane 108.

A preferred location for placement of the microphone assembly 108 is in or near the ear canal of the patient. If the hearing function of the patient is completely lost, then the microphone assembly is preferably implanted so that the microphone membrane 108 resides at the end of the ear canal where the ear drum is located. If the hearing function of the patient is not totally lost, the microphone assembly 108 may be implanted such that the membrane 5202 faces into an opening of the ear canal that is surgically made at an appropriate location along the length of the ear canal. Or, alternatively, the microphone assembly 108 may be implanted in soft tissue near the ear canal or pinna of the ear such that the membrane 5202 is positioned to sense auditory vibrations impinging on the pinna, or tissue areas near the pinna.

Suture holes 5212, located on a flange of the housing 5208, facilitate its implantation into tissue at a suitable body location, e.g., adjacent the ear canal or soft tissue near the ear.

Figure 41A:
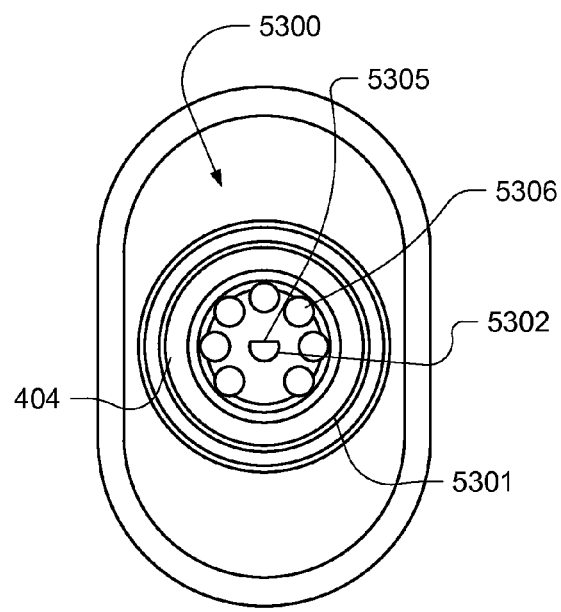
FIG. 41A illustrates a top view of an exemplary percutaneous port connector assembly, or purcuport connector, used for programming, charging the power source, and/or otherwise controlling various components included within the implanted stimulation module.

Turning next to FIG. 41A, there is shown one possible exemplary configuration of a percuport connector assembly 5300 that may be used to facilitate programming, charging of a power source, and/or otherwise controlling various components included in a percutaneous cochlear implant system of the type disclosed herein.

For charging (or recharging) of a battery included in the system, such as when a plug/connector 430 is inserted into the percuport 404 (see FIG. 4), the percuport assembly 5300 simply functions as a connector having a receiving port 5301 into which a mating connector may be inserted. The receiving port 5301 may include a pin 5302 centrally located therein, and other pins or connectors 5306, located at the bottom or side of port 5301 so as to be electrically separated and insulated from the pin 5302 and the other pins or contacts 5306. The inside wall of the receiving port 5301 may function as an additional electrical contact. For charging, a suitable mating connector is simply pushed into the receiving port 5301 of the percuport assembly 5300 so as to make electrical contact with the pin 5302 and at least one other contact 5306, such as the inner wall of the receiving port 5301, thereby allowing a suitable charging voltage and current to be applied that will replenish the power source within the implantable system.

Figure 41B:
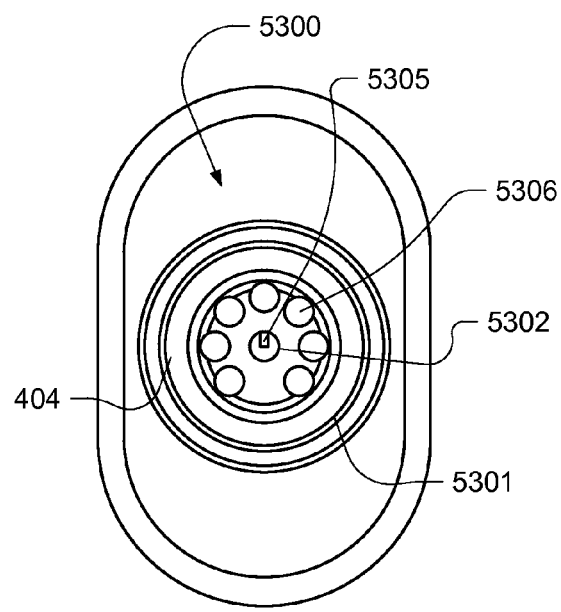
FIG. 41B illustrates a top view of an exemplary percutaneous port connector assembly as in FIG. 41A, showing an alternative technique for assuring a desired keyed relationship occurs when a plug is inserted into the connector assembly.

For programming using an external programmer, such as occurs when a plug/connector 434 (connected to an external programmer) is inserted into the percuport 404 (see FIG. 4), a keyed connection is important so that appropriate programming signals from the external programmer make contact only with prescribed contacts 5306 within the receiving port 5301 of the percuport 404. Such keyed connection can be achieved in several ways. One way is illustrated in FIG. 41A. There, a flat portion 5305 over a segment of the central pin 5302 is formed. Then, a corresponding flat portion is made in a receiving channel in the mating plug 434 that only allows it to be received into the receiving port 5301 in one orientation. Another way is illustrated in FIG. 41B. There, a slot 5303 is made in the central pin 5302. Then, a corresponding key is made in the mating plug 434 that only allows the plug it to be received into the receiving port 5301 when the key is aligned with the slot 5303.

It is noted that the contacts 5306 need not necessarily be spaced equally apart around the periphery of the bottom of the port 5301 as shown in FIG. 41A. Rather, as explained previously, see FIGS. 30-36, they may be arranged in a desired pattern that facilitates sensing rotation of a cartridge inserted into the port 5301.

For manual programming and control, using, e.g., a passive selector plug 422 inserted into the percuport 404 (see FIG. 4), the percuport connector assembly 5300 may include a passive knob/connector adapted to be inserted into the percuport's receiving port 5301. However, such passive knob connector 422 is not keyed, i.e., it does not include a flat portion or a keyed portion, and this it remains at liberty to rotate around the central pin 5302 while inserted in the receiving port 5301.

As described previously in connection with FIGS. 30-36, rotation of the knob/connector 422 (see FIG. 4) allows contacts located at a distal end of the knob/connector's barrel to selectively make and/or break contact with the contacts 5306 located in the bottom of the receiving port 5301 as the knob is rotated. Individual ones of the contacts 5311 may be connected respectively to selected other ones of the contacts 5311 so that such making and breaking of contacts can be readily detected as a sequence of opens and shorts at the contacts 5306. This sequence, or pattern, or even a particular static configuration of opens and shorts (if rotation is not occurring) can then be processed by control circuitry located in the base of the percuport 5300, or elsewhere within the percutaneous implant system, to define program and control signals. Such program and control signals may control, e.g., volume, and/or may allow a means for a user to select a sound processing program, or to turn the system on or off, simply by rotating the knob/connector 5310 within the port 5301a prescribed direction and amount.

In some embodiments, an FM module (used by school children and others) may be included within port 404 and/or otherwise communicatively coupled to sound processor 106.

The preceding descriptions of various configurations of a percutaneous cochlear implant system (PCIS) have been presented only to illustrate and describe representative embodiments of the invention. It is not intended to be exhaustive or to limit the invention to any precise form disclosed. Many modifications and variations are possible in light of the above teaching. Thus, while the invention(s) herein disclosed has (have) been described by means of specific embodiments and applications thereof, numerous modifications and variations could be made thereto by those skilled in the art without departing from the scope of the invention(s) set forth in the claims

What is claimed is:

1. A percutaneous cochlear implant system comprising:
  a cochlear stimulator configured to be coupled to an electrode lead, said electrode lead comprising a plurality of electrodes configured to be in communication with a plurality of stimulation sites within a cochlear region of a patient;
  a sound processor communicatively coupled to said cochlear stimulator and configured to direct said cochlear stimulator to generate and apply electrical stimulation representative of an audio signal to at least one of said stimulation sites via at least one of said electrodes;
  a power source configured to provide power to at least one of said cochlear stimulator and said sound processor; and
  a percutaneous port configured to be percutaneously implanted within a head of said patient and to house said power source;
  wherein said power source is configured to be rotatable, and wherein rotation of said power source is configured to adjust one or more control parameters associated with at least one of the cochlear stimulator and the sound processor.

2. The system of claim 1, wherein said power source is configured to be housed within a battery cartridge, wherein said battery cartridge comprises a control mechanism configured to facilitate manual control of said one or more control parameters.

3. A percutaneous cochlear implant system comprising:
  a cochlear stimulator configured to be coupled to an electrode lead, the electrode lead comprising a plurality of electrodes configured to be in communication with a plurality of stimulation sites within a cochlear region of a patient;
  a sound processor communicatively coupled to the cochlear stimulator and configured to direct the cochlear stimulator to generate and apply electrical stimuli representative of an audio signal to at least one of the stimulation sites via at least one of the electrodes;

a power source configured to provide operating power to at least one of the cochlear stimulator and the sound processor; and a percutaneous port configured to be percutaneously implanted within body tissue located in the head of a user of the percutaneous cochlear implant system, said percutaneous port having a plurality of feedthrough pins therein that allow direct electrical connection to be made between external components and implantable components of the cochlear implant system, and wherein the percutaneous port includes means for allowing tissue ingrowth and vascularization around its perimeter;

wherein the implantable components of the cochlear implant system comprise said cochlear stimulator, said sound processor, and said power source, and wherein said plurality of feedthrough pins within said percutaneous port provides for the direct electrical connection between at least one implanted component and at least one external component of said cochlear implant system;

wherein said power source comprises a rechargeable power source, and wherein the external components include a battery charger that connects to said rechargeable power source through a plug adapted to be removably inserted into said percutaneous port; and wherein the external components of the cochlear implant system additionally include a programmer, a diagnostic unit, and a passive selector plug, and wherein each of said external components is selectively connected to the implanted components of the cochlear implant system through a plug adapted to be removably inserted into said percutaneous port.

4. The system of claim 1, wherein said cochlear stimulator is configured to be housed within a hermetically sealed chamber attached to said percutaneous port.

5. The system of claim 4, wherein said sound processor is configured to be housed in a hermetically sealed housing that is connected to said cochlear stimulator and said percutaneous port, said hermetically sealed housing having a set of feedthrough pins attached thereto through which a microphone may be electrically connected to said sound processor.

6. A percutaneous cochlear implant system comprising:
a cochlear stimulator configured to be coupled to an electrode lead, the electrode lead comprising a plurality of electrodes configured to be in communication with a plurality of stimulation sites within a cochlear region of a patient;

a sound processor communicatively coupled to the cochlear stimulator and configured to direct the cochlear stimulator to generate and apply electrical stimuli representative of an audio signal to at least one of the stimulation sites via at least one of the electrodes;

a power source configured to provide operating power to at least one of the cochlear stimulator and the sound processor; and a percutaneous port configured to be percutaneously implanted within body tissue located in the head of a user of the percutaneous cochlear implant system, said percutaneous port having a plurality of feedthrough pins therein that allow direct electrical connection to be made between external components and implantable components of the cochlear implant system, and wherein the percutaneous port is configured to allow tissue ingrowth and vascularization around its perimeter;

wherein the implantable components of the cochlear implant system comprise said cochlear stimulator, said sound processor, and said power source, and wherein said plurality of feedthrough pins within said percutaneous port provides for the direct electrical connection between at least one implanted component and at least one external component of said cochlear implant system;

wherein said power source comprises a rechargeable power source, and wherein the external components include a battery charger that connects to said rechargeable power source through a plug adapted to be removably inserted into said percutaneous port; and wherein the external components of the cochlear implant system additionally include a programmer, a diagnostic unit, and a passive selector plug, and wherein each of said external components is selectively connected to the implanted components of the cochlear implant system through a plug adapted to be removably inserted into said percutaneous port.

7. The system of claim 6, wherein said cochlear stimulator is configured to be housed within a hermetically sealed chamber attached to said percutaneous port.

8. The system of claim 7, wherein said sound processor is configured to be housed in a hermetically sealed housing that is connected to said cochlear stimulator and said percutaneous port, said hermetically sealed housing having a set of feedthrough pins attached thereto through which a microphone may be electrically connected to said sound processor.

9. A percutaneous cochlear implant system (PCIS) comprising:
external components;
implanted components; and
a percutaneous port that provides a direct electrical interface between the external components and the implanted components of the PCIS;
said percutaneous port including a cavity therein into which external components may be removably inserted;
wherein the percutaneous port removably receives at least one component of the PCIS; and
wherein the percutaneous port removably receives a passive selector plug during operation of the PCIS, and further wherein the passive selector plug may be manually rotated within the cavity of the percutaneous port, and wherein the percutaneous port includes a sensor that senses rotation of said passive selector plug within the cavity of the percutaneous port, and wherein manual rotation of the passive selector plug is used by a user of the PCIS to manually select prescribed operating parameters of the PCIS.

10. A method of configuring a cochlear stimulation system comprising:
providing an implantable cochlear stimulator configured to be coupled to an implantable electrode lead, said implantable electrode lead comprising a plurality of electrodes configured to be in communication with a plurality of stimulation sites within a cochlear region of a patient;

providing a sound processor communicatively coupled to said cochlear stimulator and configured to direct said cochlear stimulator to generate and apply electrical stimulation representative of an audio signal to at least one of said stimulation sites via at least one of said electrodes;

providing a power source configured to provide power to at least one of said cochlear stimulator and said sound processor;

configuring a percutaneous port so as to sense directional rotation of a member inserted therein;

percutaneously implanting said percutaneous port within head tissue of a user of said cochlear stimulation system;

connecting said power source to said implantable cochlear stimulator through said percutaneous port by removably inserting said power source within said percutaneous port, said percutaneous port having a cavity that receives said power source and that allows said power source to be rotated while inserted therein; and sensing the rotation of the power source inserted within said percutaneous port as a way of manually selecting specified parameters associated with the operation of said cochlear stimulator system.

11. The method of claim 10, further comprising:

connecting said sound processor to said implantable cochlear stimulator through said percutaneous port.

* * * * *